United States Patent
Selander et al.

(10) Patent No.: US 12,048,533 B2
(45) Date of Patent: Jul. 30, 2024

(54) EVALUATION OF DATA TO PROVIDE DECISION SUPPORT FOR A KETOGENIC LIFESTYLE

(71) Applicant: DexCom, Inc., San Diego, CA (US)

(72) Inventors: Mark Edward Selander, San Diego, CA (US); Alexander Michael Diener, San Diego, CA (US); Ryan Richard Ruehl, San Diego, CA (US); Kazanna Calais Hames, San Diego, CA (US); Mark Douglas Kempkey, Vista, CA (US); Chad Michael Patterson, San Diego, CA (US); Apurv Ullas Kamath, San Diego, CA (US); Matthew Lawrence Johnson, Solana Beach, CA (US); Jason M. Halac, Solana Beach, CA (US); David A. Price, Carlsbad, CA (US); Peter C. Simpson, Cardiff, CA (US); Devon M. Headen, Atlanta, GA (US); Samuel Isaac Epstein, Chevy Chase, MD (US)

(73) Assignee: Dexcom, Inc., San Diego, CA (US)

( * ) Notice: Subject to any disclaimer, the term of this patent is extended or adjusted under 35 U.S.C. 154(b) by 276 days.

(21) Appl. No.: 17/188,675

(22) Filed: Mar. 1, 2021

(65) Prior Publication Data
US 2021/0267506 A1 Sep. 2, 2021

Related U.S. Application Data

(60) Provisional application No. 62/984,238, filed on Mar. 2, 2020.

(51) Int. Cl.
*A61B 5/145* (2006.01)
*A61B 5/00* (2006.01)
(Continued)

(52) U.S. Cl.
CPC ........ *A61B 5/14546* (2013.01); *A61B 5/1118* (2013.01); *A61B 5/14532* (2013.01);
(Continued)

(58) Field of Classification Search
CPC .............. A61B 5/14546; A61B 5/1118; A61B 5/14532; A61B 5/165; A61B 5/7246; A61B 5/7275; A61B 5/7475; G16H 20/60
See application file for complete search history.

(56) References Cited

U.S. PATENT DOCUMENTS

| 6,001,067 A | 12/1999 | Shults et al. |
| 2006/0020187 A1 | 1/2006 | Brister et al. |

(Continued)

OTHER PUBLICATIONS

Fletcher, Lauren, et al. "Feasibility of an implanted, closed-loop, blood-glucose control device." Immunology 230. (Year: 2001).*

(Continued)

*Primary Examiner* — Marjan Fardanesh
(74) *Attorney, Agent, or Firm* — Patterson + Sheridan, LLP

(57) ABSTRACT

Techniques for data analysis and user guidance are provided. One or more current measurements of one or more current analyte levels for the user are received from a sensor. A pattern is generated based on the one or more current measurements and the one or more past measurements. A first alignment with a first user target is then determined based on the pattern, where the first user target relates to one or more of a mental state or physical state of the user. A first result is output to the user, based on the determined first alignment.

20 Claims, 8 Drawing Sheets

(51) Int. Cl.
    *A61B 5/11*          (2006.01)
    *A61B 5/16*          (2006.01)
    *G16H 20/60*       (2018.01)

(52) U.S. Cl.
    CPC ............ *A61B 5/165* (2013.01); *A61B 5/7246* (2013.01); *A61B 5/7275* (2013.01); *A61B 5/7475* (2013.01); *G16H 20/60* (2018.01)

(56) References Cited

U.S. PATENT DOCUMENTS

| | | |
|---|---|---|
| 2007/0027385 A1 | 2/2007 | Brister et al. |
| 2009/0137887 A1 | 5/2009 | Shariati et al. |
| 2011/0027127 A1 | 2/2011 | Simpson et al. |
| 2014/0095081 A1 | 4/2014 | Doniger et al. |
| 2015/0025811 A1 | 1/2015 | Kodama et al. |
| 2015/0173648 A1 | 6/2015 | Sano et al. |
| 2017/0332951 A1 | 11/2017 | Ahmad et al. |
| 2018/0256103 A1* | 9/2018 | Cole ..................... A61B 5/742 |
| 2018/0263541 A1 | 9/2018 | Kodama et al. |
| 2019/0096281 A1 | 3/2019 | Ahmad et al. |
| 2019/0254592 A1 | 8/2019 | Ahmad et al. |
| 2019/0295723 A1 | 9/2019 | Bill |

OTHER PUBLICATIONS

International Search Report and Written Opinion dated May 21, 2021 for Application No. PCT/US2021/020278, filed Mar. 1, 2021; 7 pages.

\* cited by examiner

EVALUATION OF DATA TO PROVIDE DECISION SUPPORT FOR A KETOGENIC LIFESTYLE

CROSS-REFERENCE TO RELATED APPLICATIONS

This application claims the benefit of U.S. Application Ser. No. 62/984,238 entitled "EVALUATION OF DATA TO PROVIDE DECISION SUPPORT FOR A KETOGENIC LIFESTYLE," which was filed on Mar. 2, 2020, which is herein incorporated by reference in its entirety.

BACKGROUND

Field

This application relates generally to medical devices. More specifically, this application relates to techniques for using data collected by one or more devices to provide support for user decision-making for a ketogenic lifestyle.

Description of the Related Technology

Increasingly, individuals have sought to manage their diet and activity to enjoy a healthy life. Some individuals have pursued a ketogenic diet, causing their bodies to enter ketosis, which is a state when the body is metabolizing fat rather than glucose. To do so, individuals must carefully control their diet (typically by ingesting food and drink that is high in fat and low in carbohydrates). While in ketosis, ketones are manufactured in the liver of the individual. Ketones are compounds created in the liver when fat (as opposed to glucose) is processed to provide the necessary energy for living tissue. The level of ketones for an individual can be used to determine whether the individual is in ketosis. While maintaining ketosis, many individuals report experiencing a wide variety of health benefits, including lower blood sugar and insulin levels, improved insulin sensitivity, weight loss, better diabetes management such as via lower or no insulin dependency for type 2 diabetes, improved heart health, reduced cancer and epilepsy risk, reduced acne, improved brain function such as improved focus and/or learning, treatment for disease such as Parkinson's, Alzheimer's, sleep disorders, etc., help with polycystic ovary syndrome, etc.

SUMMARY

According to certain embodiments of the present disclosure, a system is provided. The system includes one or more sensors configured to detect one or more current analyte levels for a user, wherein the one or more current analyte levels are correlated to a current level of ketones of the user; a memory circuit storing one or more past measurements of one or more past analyte levels for the user, wherein the one or more past analyte levels are correlated to one or more past levels of ketones of the user; and a processor configured to perform an operation. The operation includes receiving, from the sensor, one or more current measurements of the one or more current analyte levels for the user; generating a pattern based on the one or more current measurements and the one or more past measurements; determining a first alignment with a first user target based on the pattern, wherein the first target relates to one or more of a mental state or physical state of the user; and outputting a first result to the user, based on the determined first alignment.

According to certain embodiments of the present disclosure, the one or more current analyte levels comprise one or more of a glucose level, a lactate level, or a ketone level.

According to certain embodiments of the present disclosure, the first result comprises a recommendation of an action.

According to certain embodiments of the present disclosure, the recommendation of an action is one or more of a recommendation to refrain from eating one or more foods, a recommendation to eat one or more foods, a recommendation to partake in one or more activities, or a recommendation to refrain from one or more activities.

According to certain embodiments of the present disclosure, the first result comprises a user interface indicating one or more of a current ketone state of the user or a predicted future ketone state of the user.

According to certain embodiments of the present disclosure, the first result comprises a user interface indicating one or more of a current weight of the user or a predicted future weight of the user.

According to certain embodiments of the present disclosure, the first result comprises a user interface indicating one or more of a current mental state of the user or a predicted future mental state of the user.

According to certain embodiments of the present disclosure, the operation further comprises: refining the pattern based on the one or more current measurements; receiving one or more additional measurements of one or more additional analyte levels for the user; and determining a second alignment with the first user target based on the refined pattern.

According to certain embodiments of the present disclosure,

According to certain embodiments of the present disclosure, the one or more past measurements are correlated with one or more past mental states, wherein the first target relates to the mental state, and wherein the first result comprises a predicted mental state of the user.

According to certain embodiments of the present disclosure, the one or more past measurements are correlated with one or more past weights, wherein the first target relates to weight of the user, and wherein the first result comprises a predicted weight of the user.

According to certain embodiments of the present disclosure, the operation further comprises receiving an indication of a physical activity associated with the user, wherein generating the pattern is further based on the indication of the physical activity.

According to certain embodiments of the present disclosure, the first user target is a ketone level.

According to certain embodiments of the present disclosure, the first result indicates whether or not the first user target is predicted to be met at a future time.

According to certain embodiments of the present disclosure, generating the pattern comprises: determining a rate of change of one or more analyte levels of the user, based on the one or more current measurements and the one or more past measurements; generating a trend line for the user, based on the determined rate of change; and estimating a future state of the user, based on the trend line.

According to certain embodiments of the present disclosure, the operation further comprises identifying a plurality of user targets associated with the user, wherein the plurality of user targets comprises user-specified targets with respect to (i) weight loss, (ii) mental health, (iii) glucose level, (iv) insulin sensitivity, and (v) glucose sensitivity.

According to certain embodiments of the present disclosure, determining the first alignment with the first user target comprises: determining whether a current state of the user aligns with the first target; and determining whether a predicted future state of the user aligns with the first target.

According to certain embodiments of the present disclosure, the operation further comprises upon determining that the predicted future state of the user does not align with the first target, generating a first recommendation, wherein the first recommendation includes an action that will increase a probability that the predicted future state will align with the first target, wherein the first result comprises the first recommendation.

According to certain embodiments of the present disclosure, a computer-implemented method is provided. The method includes receiving, from a sensor, one or more current measurements of one or more current analyte levels for the user; generating a pattern based on the one or more current measurements and the one or more past measurements; determining a first alignment with a first user target based on the pattern, wherein the first target relates to one or more of a mental state or physical state of the user; and outputting a first result to the user, based on the determined first alignment.

According to certain embodiments of the present disclosure, the method further comprises refining the pattern based on the one or more current measurements; receiving one or more additional measurements of one or more additional analyte levels for the user; and determining a second alignment with the first user target based on the refined pattern.

According to certain embodiments of the present disclosure, generating the pattern comprises: refining the pattern based on the one or more current measurements; receiving one or more additional measurements of one or more additional analyte levels for the user; and determining a second alignment with the first user target based on the refined pattern.

According to certain embodiments of the present disclosure, a non-transitory computer-readable storage medium is provided. The computer-readable storage medium is encoded with instructions operable to configure an electronic device to perform an operation. The operation includes receiving, from a sensor, one or more current measurements of one or more current analyte levels for the user; generating a pattern based on the one or more current measurements and the one or more past measurements; determining a first alignment with a first user target based on the pattern, wherein the first target relates to one or more of a mental state or physical state of the user; and outputting a first result to the user, based on the determined first alignment.

According to certain embodiments of the present disclosure, the operation further comprises: refining the pattern based on the one or more current measurements; receiving one or more additional measurements of one or more additional analyte levels for the user; and determining a second alignment with the first user target based on the refined pattern.

Another aspect is a system comprising: a sensor configured to detect one or more current analyte levels for a user, wherein the one or more current analyte levels are correlated to a current level of ketones of the user; a memory circuit storing one or more past measurements of one or more past analyte levels for the user, wherein the one or more past analyte levels are correlated to one or more past levels of ketones of the user; and a processor in data communication with the sensor and the memory circuit, the processor configured to: receive, from the sensor, one or more current measurements of the one or more current analyte levels for the user; generate a pattern based on the one or more current measurements received from the sensor and the one or more past measurements stored in the memory circuit; determine a first alignment with a first user target based on the generated pattern, wherein the first user target relates to one or more of a mental state or physical state of the user; and output a first result to the user, based on the determined first alignment.

In the above system, the one or more current analyte levels comprise one or more of a glucose level, a lactate level, or a ketone level. In the above system, the first result comprises a recommendation of an action. In the above system, the recommendation of the action comprises one or more of a recommendation to refrain from eating one or more foods, a recommendation to eat one or more foods, a recommendation to partake in one or more activities, or a recommendation to refrain from one or more activities.

In the above system, the processor is configured to output the first result in a user interface indicating one or more of a current ketone state of the user or a predicted future ketone state of the user. In the above system, the processor is configured to output the first result in a user interface indicating one or more of a current weight of the user or a predicted future weight of the user. In the above system, the processor is configured to output the first result in a user interface indicating one or more of a current mental state of the user or a predicted future mental state of the user.

In the above system, the processor is further configured to: refine the pattern based on the one or more current measurements; receive one or more additional measurements of one or more additional analyte levels for the user; and determine a second alignment with the first user target based on the refined pattern.

In the above system, the one or more past measurements are correlated with one or more past mental states, wherein the first user target relates to the mental state, and wherein the first result comprises a predicted mental state of the user. In the above system, the processor is further configured to: receive an indication of a physical activity associated with the user; and generate the pattern further based on the indication of the physical activity.

In the above system, the first user target relates to a ketone level. In the above system, the first result indicates whether or not the first user target is predicted to be met at a future time. In the above system, to generate the pattern, the processor is configured to: determine a rate of change of one or more analyte levels of the user, based on the one or more current measurements and the one or more past measurements; generate a trend line for the user, based on the determined rate of change; and estimate a future state of the user, based on the trend line.

In the above system, the processor is further configured to: identify a plurality of user targets associated with the user, wherein the plurality of user targets comprise user-specified targets with respect to (i) weight loss, (ii) mental health, (iii) glucose level, (iv) insulin sensitivity, and (v) glucose sensitivity. In the above system, to determine the first alignment with the first user target, the processor is configured to: determine whether a current state of the user aligns with the first user target; and determine whether a predicted future state of the user aligns with the first user target.

In the above system, the processor is further configured to: in response to determining that the predicted future state of the user does not align with the first user target, generate a first recommendation, wherein the first recommendation includes an action that will increase a probability that the predicted future state will align with the first user target, and wherein the first result comprises the first recommendation.

Another aspect is a computer-implemented method, comprising: receiving, at a processor, one or more current measurements of one or more current analyte levels for a user from a sensor; storing, at a memory circuit, one or more past measurements of one or more past analyte levels for the user, wherein the one or more past analyte levels are correlated to one or more past levels of ketones of the user; generating, at the processor, a pattern based on the one or more current measurements received from the sensor and the one or more past measurements stored in the memory circuit; determining, at the processor, a first alignment with a first user target based on the generated pattern, wherein the first user target relates to one or more of a mental state or physical state of the user; and outputting, at the processor, a first result to the user, based on the determined first alignment.

The above method further comprises: refining the pattern based on the one or more current measurements; receiving one or more additional measurements of one or more additional analyte levels for the user; and determining a second alignment with the first user target based on the refined pattern. In the above method, generating the pattern comprises: determining a rate of change of one or more analyte levels of the user, based on the one or more current measurements and the one or more past measurements; generating a trend line for the user, based on the determined rate of change; and estimating a future state of the user, based on the trend line.

Another aspect is a non-transitory computer-readable storage medium encoded with instructions operable to configure an electronic device to perform an operation, the operation comprising: receiving, at a processor, one or more current measurements of one or more current analyte levels for a user from a sensor; storing, at a memory circuit, one or more past measurements of one or more past analyte levels for the user, wherein the one or more past analyte levels are correlated to one or more past levels of ketones of the user; generating, at the processor, a pattern based on the one or more current measurements received from the sensor and the one or more past measurements stored in the memory circuit; determining, at the processor, a first alignment with a first user target based on the pattern, wherein the first user target relates to one or more of a mental state or physical state of the user; and outputting, at the processor, a first result to the user, based on the determined first alignment.

Any of the features of an aspect is applicable to all aspects identified herein. Moreover, any of the features of an aspect is independently combinable, partly or wholly with other aspects described herein in any way, e.g., one, two, or three or more aspects may be combinable in whole or in part. Further, any of the features of an aspect may be made optional to other aspects. Any aspect of a method can comprise another aspect of a system, and any aspect of a system can be configured to perform a method of another aspect.

DETAILED DESCRIPTION

Problem

Figure 1:
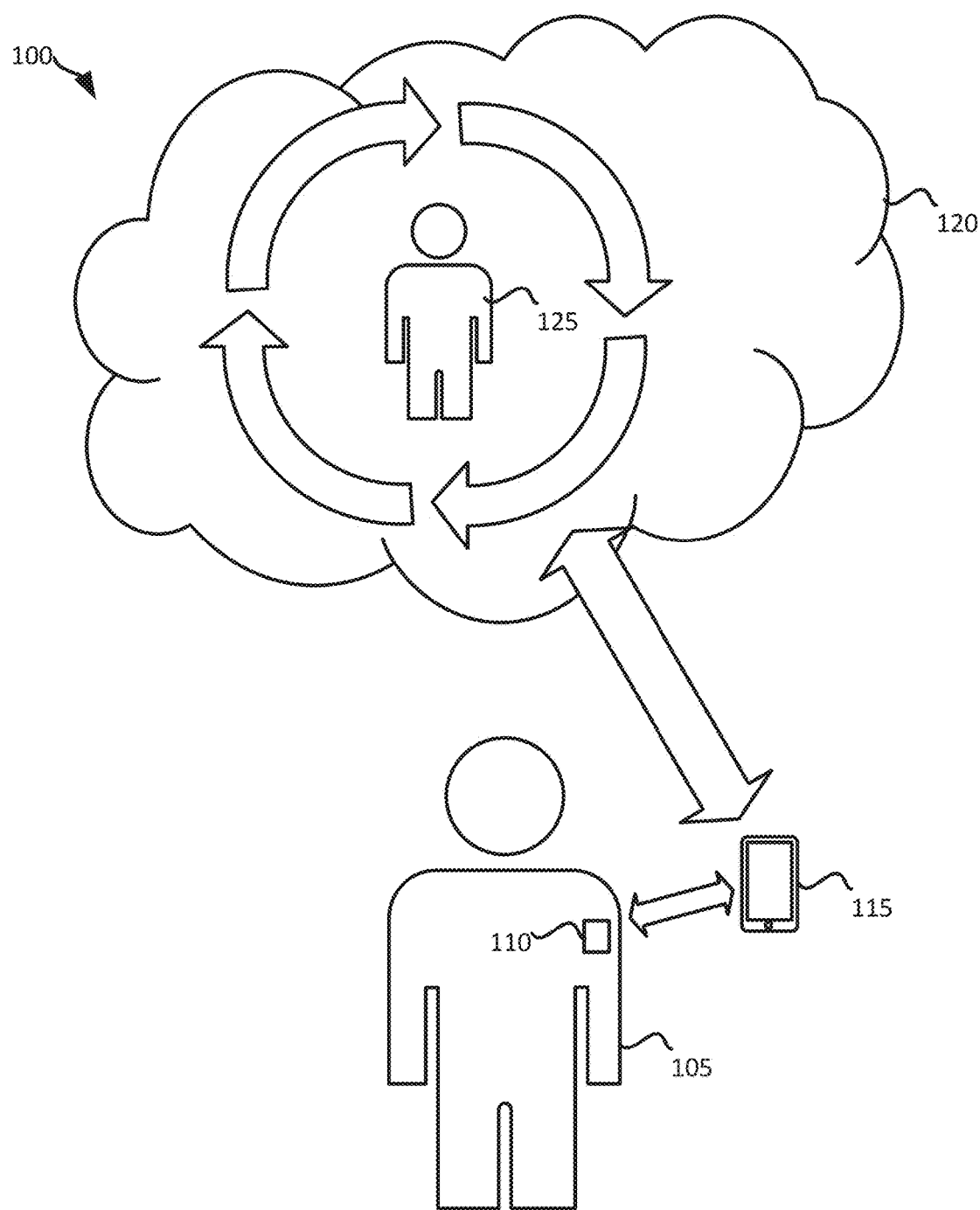
FIG. 1 illustrates an ecosystem for collection and analysis of data to guide user decision-making, according to certain embodiments disclosed herein.

Maintaining ketosis, however, often requires a delicate balance. If too many ketones are present in the blood, ketoacidosis can result, which is a potentially life threatening metabolic state. If too few ketones are present, the individual will experience reduced (or eliminated) health benefits, as compared to the optimal range. The optimal range of ketones differs significantly for individual users based on any number of biological factors, making it difficult or impossible to maintain ketosis. Further, it is difficult or impossible to determine what foods to ingest (as well as the proper amount of food) and what activities to participate in to maintain a desired ketosis level.

Additionally, there are a large number of other risks and drawbacks with ketogenic diets. For many, the diet is unsustainable or very difficult to follow. For example, because the diet typically requires ingestion of very little carbohydrates, the vast majority (upwards of seventy-five percent) of the user's calories are ingested via fats. Typically, individuals today rely on a much wider variety of foods, including breads, fruits, meats, and vegetables to build a balanced diet and satisfy their cravings. Limiting oneself to a much narrower diet is difficult and frustrating.

Further, eliminating the typical foods individuals enjoy can cause a number of physiological and mental distresses. Often referred to as the "keto flu," individuals frequently experience symptoms including fatigue, headaches, difficulty with attention, aches, and general frustrations when beginning the diet. Although these symptoms are usually temporary and only manifest during the transition to a ketogenic diet, they are nevertheless significantly impactful, and cause many to give up on the diet plan before they begin to achieve the full benefits.

Moreover, if the user successfully enters ketosis, it can be difficult or impossible to maintain. A large portion of foods typically enjoyed are no longer allowable, which can significantly reduce the individual's ability to maintain the diet. For example, in social settings, it can be difficult or impossible to identify appropriate food options. Additionally, the complexity of the diet can cause the individual to feel mocked or scorned by their peers, as they are so limited in what they can consume.

In addition, even if ketosis is maintained, if an individual makes poor choices in diet for maintaining ketosis, such as selecting foods with a high saturated fat content, it could have other adverse health effects, such as increasing LDL cholesterol in the body, which has been known to cause heart and other health complications.

Although ketogenic diets show notable promise to improve the short and long term health of individuals, the complexity and restrictiveness of the diet coupled with the potential for significant physical and mental difficulty can prevent a large number of individuals from benefitting from the diet.

For many, ketosis is a highly desirable state, as it can lead to weight loss, improved insulin resistance or sensitivity and glucose sensitivity, reduced acne, and improved heart health. Ketosis has also been linked to a number of other therapeutic benefits, with respect to a number of conditions including cancer, epilepsy, diabetes, and endocrine and metabolic disorders. A significant contributor to ketosis is the diet of the user. Some existing solutions have attempted to provide information to users to help guide them to ketosis using predefined allowable and disallowed food options. However, these lists are static and not personalized, causing them to fall far short for many. For example, although one may estimate the impact of a given food for a general population, existing systems cannot account for how a given food interacts with other food the user has consumed, activities the user has engaged in, and the like.

Furthermore, existing solutions fail to address the needs and uniqueness of the individual. A simple static list of "keto-friendly" recipes cannot account for the fact that different individuals often respond to the same food in different ways. This different response can be based on a wide variety of factors, including the demographics of the individual. In certain embodiments, the demographics of the individual can include, for example, their gender, age, ethnicity, and the like. Further, the differing responses are often due to unseen factors, including the genetics and activity of the user. Moreover, simple factors like the time of day can impact how a meal influences the user's ketone levels. Existing systems simply cannot account for these factors.

Additionally, existing systems do not understand and respond to activities of the user. For example, different exercises and activities can cause vastly different impacts on ketone levels. The intensity, duration, and timing of the exercise can significantly affect ketone levels, but existing systems often ignore these factors. Even if advice is given with respect to physical activities, existing systems rely on broad generalizations rather than specific, individualized, and science-based coaching.

Moreover, existing systems typically rely on minimal and infrequent measurements, which dramatically reduces the success individuals can achieve. For example, existing techniques typically rely on manual blood testing by the user at relatively infrequent times. Even if the user performs the tests on time, the data is often outdated and useless by the time it is returned. Further, users frequently skip such evaluations for a variety of reasons such as convenience and absentmindedness.

Overview of General Solution

Ultimately, these factors and others cause ketosis to be a difficult state to reach and/or maintain, requiring highly complex decision making that typical users simply cannot perform. The number and variety of factors and decisions quickly overwhelm, and the paucity of hard data to track the user's status in real-time causes a large number of individuals to give up entirely. To that end, certain embodiments of the present disclosure provide techniques to actively and continuously monitor analyte levels correlated to ketone levels in users and provide one or more results based on the monitoring. The results may be user specific and provided based on real-time data to better inform the user of their ketone levels. The results may even provide suggested actions for the user to better lead a ketogenic lifestyle.

In certain embodiments, the analyte is one or more of ketone, glucose, and/or lactate. Furthermore, although the description herein refers to one or more of ketone, glucose, and/or lactate as the analytes being measured, processed, and the like, other analytes may be used as well. In certain embodiments, the other analytes can include, for example, acetone, acetoacetic acid, beta hydroxybutyric acid, glucagon, acetyl-CoA, triglycerides, fatty acids, intermediaries in the citric acid cycle, choline, insulin, cortisol, testosterone, and the like. For example, different analytes may be correlated with ketone levels. For example, glucose levels are correlated with ketone levels. Further, lactate levels are correlated with ketone levels.

In certain embodiments, the results include one or more of current analyte level, predicted analyte level, current ketone level, future ketone level, current state, and/or future state. In certain embodiments, current state and/or future state may be a ketone state indicating whether or not the user is in ketosis. In certain embodiments, current state and/or future state may be a mental and/or physical state of the user. For example, a physical state may be one or more of a weight, a disease state, an insulin resistance or sensitivity, a glucose sensitivity, etc. In certain embodiments, the present disclosure provides techniques to, based on the monitored analyte levels, provide recommendations to a user to achieve and/or maintain a desired state. In some embodiments, the desired state may be a specific ketone, glucose or lactate level or other analyte level. In certain embodiments, the desired ketone state is ketosis. In other embodiments, the desired state may be a disease state. In certain embodiments, recommendations can be one or more of recommended actions, recommended inactions, encouragement, alarms, etc. In certain embodiments, the results include cumulative data as monitored. In certain embodiments, the results include displays of data as discussed herein.

For example, in certain embodiments, based on the current analyte level of a user, a determination module is used to determine current state. Further, in certain embodiments, the determination module is used to determine predicted future states. In certain embodiments, the states indicate whether or not a user is reaching a desired state (e.g., in ketosis). In certain embodiments, the module generates one or more patterns indicative of predicted future state of a user. In certain embodiments, the one or more patterns include one or more of data models, rate of change, trend lines, or the like. In certain embodiments, the one or more patterns are generated using one or more of computer modeling, machine learning, pattern identification, a bolus calculator, a function, or an algorithm. In some embodiments, the system utilizes user-specific data to generate the one or more patterns associated with a user. For example, the system may continuously collect data such as analyte levels to generate the one or more patterns.

In certain embodiments, the system may collect data regarding actions performed by the user to refine the one or more patterns. For example, various actions, such as physical activity can affect ketone and/or other analyte levels. For example, in certain embodiments, actions include one or more of physical activity, consumption of food and/or beverages, contextual information, and the like. In certain embodiments, the user provides the information via input on the user device. This can allow the system to build more robust patterns that can predict how particular foods, drinks, and physical activities will impact the user's ketone or other analyte levels.

Further, in at least one embodiment, the system additionally collects information relating to the user's state. For example, the user can report their current level of hunger, mental state, physical state, and the like. In another example, current user states may be determined based on monitoring user health or activity information using various sensors or input devices. In certain embodiments, various inputs to the system can include data collected from one or more of activity trackers, glucose meters, insulin meters, and the like. For example, the data can include one or more of a number of steps taken by the user, a heart rate of the user, a blood pressure of the user, a glucose level of the user, an insulin level of the user, an electrocardiogram (ECG) of the user, and the like. In some embodiments, the input data can include information from meal logs associated with the user. For example, the user may log indications of food and/or beverages they consumed. In some embodiments, the meal information includes indications of one or more of the type of food, the quantity of food, the nutritional content of the food, and the like. This meal information can be used to determine the state of the user. In certain embodiments, the input data can include data from cameras or other devices located on or near the user. For example, a camera can be used to record images of meals the user consumed and/or is consuming. These images can then be analyzed to identify the meals and quantities being consumed. This information can further aid the determination of the user's state.

In certain embodiments, the mental state can include, for example, whether they feel annoyed, content, anxious, and the like. Using this data, the system is better able to predict the state of the user in the future, given one or more of current analyte measurements, one or more past analyte measurements, and/or one or more actions. For example, in certain embodiments, the system may learn that, given current analyte levels, the user is likely feeling hungry at the moment, but that if the user refrains from eating, the hunger will subside and ketosis will be maintained.

In certain embodiments, the system may collect data regarding mental states of the user and correlate the mental states with the analyte levels. For example, the system may generate a pattern for mental state that is correlated with analyte levels. For example, the correlated mental states may be used to predict future mental state of the user based on a predicted future analyte levels. The system may, in certain embodiments, correlate other physical states with the analyte levels. In certain aspects, the system predicts future physical states of the user based on predicted future analyte levels. For example, the system may generate one or more patterns for one or more physical states that are correlated with analyte levels.

Further, certain embodiments identify one or more actions to ensure that a desired state is achieved or maintained. In one example, the desired state may include a desired physical state. For example, one or more actions may be identified to reach a Ketone state of ketosis. In another example, one or more actions may be identified to ensure that a ketone state of ketosis is preserved based on the one or more patterns, and/or that a particular mental state is achieved. In certain embodiments, the one or more actions include one or more of consuming certain foods, refraining from consuming certain foods, partaking in certain physical activities, refraining from partaking in certain physical activities, and the like. In certain embodiments, instead of ensuring the ketone state of ketosis is preserved, the one or more actions may increase the probability that a desired physical or mental state is achieved and maintained. The one or more actions may be identified to ensure a preferred state in an order of preference. In some embodiments, a user may indicate preference for different physical and/or mental states independently or in relation to other desired states and action suggestions may be prioritized or provided accordingly. For example, a user may indicate that a certain desired mental state is more important than achieving a certain physical state (e.g., ketosis), or vice versa, and an action is suggested accordingly.

In certain embodiments, the system can further integrate with a variety of other devices that provide measurements of other data, such as one or more of weight, heart rate, blood pressure, activity levels, analyte levels, etc. In certain embodiments, the other devices include one or more of weight trackers, heart beat/rate monitors, or other sensors. These measurements can then be provided to the system that generates the one or more patterns. The measurements may be correlated with the one or more patterns. Accordingly, in certain embodiments, the one or more patterns can be used, based on the correlated measurements, to one or more of predict future states of the user, or to recommend one or more actions. In some embodiments, the system executes at least partially in the cloud. In another embodiment, the system executes at least partially on one or more local devices. In certain embodiments, one or more local devices include a smart phone of the user. In certain embodiments, the system is able to identify patterns and make correlations that allow it to return personalized recommendations that account for how the body of the specific user will react to specific actions.

Advantageously, embodiments of the present disclosure can dynamically generate and refine one or more patterns that allow for improved results for users. In some embodiments, an ecosystem of devices interact to jointly improve the functionality of each device and the ecosystem overall. For example, analyte sensors can be used to return real-time or near real-time data to a determination module, in order to deliver new functionality that is not possible with current systems. In certain embodiments, the new functionality can include higher resolution data evaluation and response. Further, the specialized patterns and/or correlations can provide new and unconventional insights for individual users, resulting in better experiences.

Overview of an Example System and Operation of the System

FIG. 1 illustrates an ecosystem 100 for collection and analysis of data to guide user decision-making, according to certain embodiments disclosed herein. In the illustrated embodiment, an intelligent System 120 utilizes a Sensor 110 and/or Device 115 associated with a User 105 to build one or more Patterns 125. The Sensor 110, in certain embodiments, is configured to measure levels of one or more analytes as discussed herein and transfer information indicative of the one or more analyte levels to the Device 115. In certain aspects, the Device 115, based on the one or more analyte levels, is configured to generate one or more Patterns 125 indicative of one or more of predicted ketone level of the user, predicted mental state of the user, or predicted physical state of the user. In certain aspects, Device 115 builds the one or more Patterns 125 locally. In certain aspects, the Device 115 and/or the sensor 110 directly sends information to a cloud system, and the cloud system builds the one or more Patterns 125. The Device 115, in certain embodiments, is further configured to process the one or more Patterns 125 and provide useful results to the User 105. Functionality of the ecosystem 100 is described in more detail with respect to the flow diagram of FIG. 2 illustrating functionality of ecosystem 100 in certain embodiments.

Figure 2:
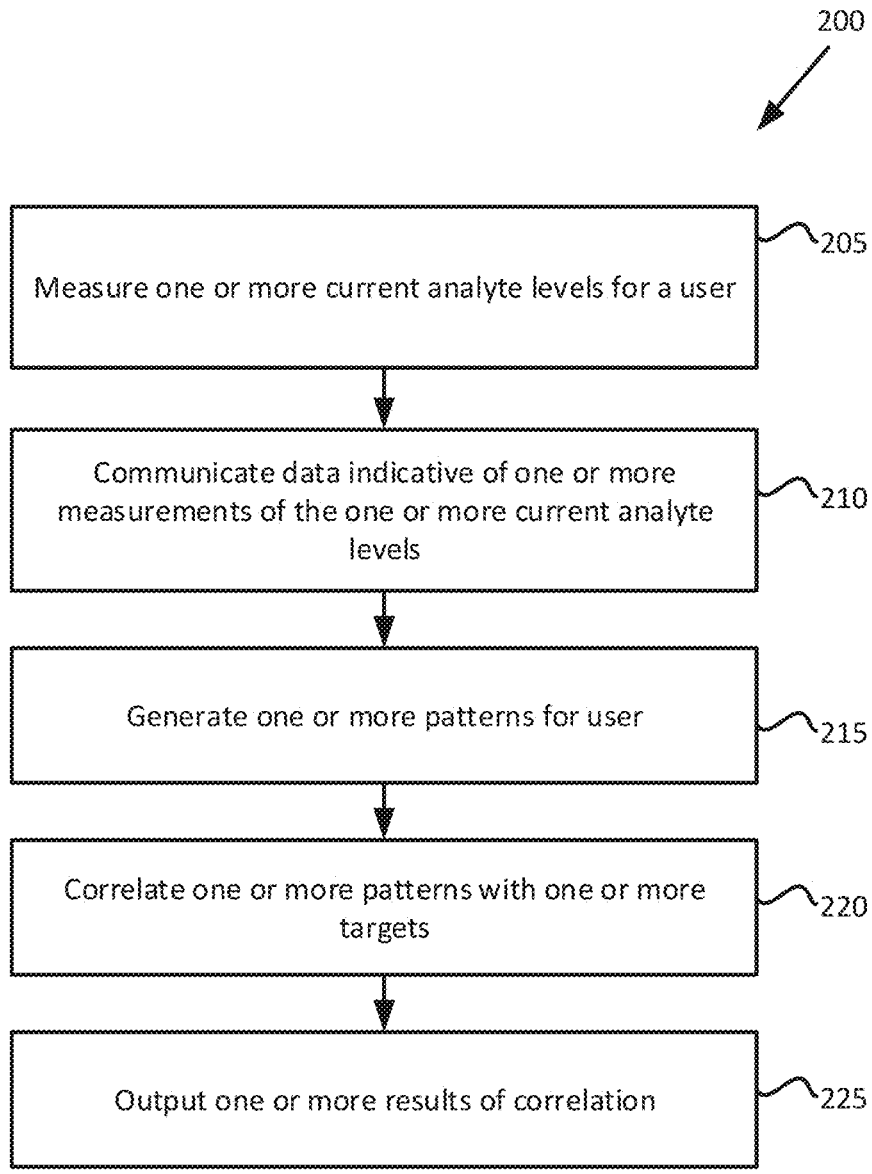
FIG. 2 is a flow diagram illustrating a method for collection and analysis of data to guide user decision-making, according to certain embodiments disclosed herein.

FIG. 2 is a flow diagram illustrating a method 200 for collection and analysis of data to guide user decision-making, according to certain embodiments disclosed herein. Note that the blocks of the method 200 may not necessarily be performed in the order described herein. Furthermore, some blocks or states herein may be omitted, and/or additional blocks or states may be added. The method 200 begins at block 205, where Sensor 110 measures one or more current analyte levels for a user. In certain embodiments, the one or more current analyte levels are correlated to a current level of ketones of the user, as discussed.

Further, at block 210, the Sensor 110 communicates data indicative of one or more current measurements of the one or more current analyte levels to Device 115. In certain embodiments, the Device 115 may further communicate the one or more current measurements to another device, such as a cloud system, for further analysis. In certain embodiments, the further analysis is performed locally on the Device 115. In certain embodiments, the further analysis is performed on the cloud system and results sent to Device 115. In certain embodiments, the further analysis is jointly performed by the Device 115 and one or more additional devices. Accordingly, certain steps of analysis are described further as being performed by Device 115 for ease of understanding and brevity, however, it should be noted that such steps of analysis may be performed by one or more other devices in addition to or alternative to Device 115.

Continuing, at block 215, Device 115, based on the one or more current measurements, and based on one or more past measurements of analyte levels received by Device 115 from Sensor 110, generates one or more Patterns 125. In certain embodiments, the one or more Patterns 125, as will be discussed, are indicative of one or more of current or predicted ketone level of the user, predicted mental state of the user, or predicted physical state of the user in the future. In certain embodiments, the one or more Patterns 125 include one or more of data models, rate of change, trend lines, or the like. In certain embodiments, the one or more Patterns 125 are generated using one or more of computer modeling, machine learning, pattern identification, a bolus calculator, a function, or an algorithm. In certain embodiments, the Device 115 further collects additional data correlated with the one or more current measurements and/or one or more past measurements in order to generate the one or more Patterns 125. For example, the additional data, in certain embodiments, includes one or more of physical state data or mental state data of the user.

Further, at block 220, Device 115 correlates the one or more Patterns 125 with one or more targets. The one or more targets, in certain embodiments, are User 105 defined, such as via Device 115. In certain embodiments, the one or more targets include a ketone range associated with being in ketosis, as will be discussed. In another example, the ketone range may be user specific, such as based on demographics of the user and demographic data collected over time and processed to determine a user-specific ketone range associated with being in ketosis. The one or more targets, in certain embodiments, include one or more of a desired physical state or mental state of User 105.

At block 225, Device 115 outputs one or more results of the correlation to User 105. For example, Device 115 indicates if the one or more targets are met. In certain embodiments, Device 115 provides recommendations to help User 105 achieve the one or more targets, or maintain the one or more targets. In certain embodiments, Device 115 provides information regarding the correlation and/or measured analyte levels to User 105.

Each of the various blocks of method 200 is described in further specificity and detail herein, with respect to various embodiments.

Sensor and Analyte Measurement

Sensor 110 is configured to measure one or more analytes correlated with ketones. In certain embodiments, the one or more analytes are one or more of ketone, glucose, and/or lactate. Furthermore, although the description herein refers to one or more of ketone, glucose, and/or lactate as the analytes being measured, processed, and the like, other analytes may be used as well including, for example, acetone, acetoacetic acid, beta hydroxybutyric acid, glucagon, acetyl-CoA, triglycerides, fatty acids, intermediaries in the citric acid cycle, choline, insulin, cortisol, testosterone, and the like. For example, different analytes may be correlated with ketone levels. For example, glucose levels may be correlated with ketone levels. Further, lactate levels are correlated with ketone levels. For example, the System 120 may use predefined correlations or algorithms, and/or user-specific models, to estimate values for some analytes. In some embodiments, given glucose and/or lactate measurements, the System 120 can infer ketone levels.

In certain embodiments, Sensor 110 is configured to measure a single analyte. In certain embodiments, Sensor 110 is configured to measure multiple analytes. In certain embodiments, although a single Sensor 110 is depicted, in some embodiments, there may be any number of Sensors 110 in use by a given User 105.

In certain embodiments, Sensor 110 is an implantable or ingestible device configured to operate within the body of the User 105. In certain embodiments, the Sensor 110 can also include a wearable device, handheld devices, and the like. In certain embodiments, wearable devices can include devices attached to the skin of the User 105 or worn on the body of the User 105. In certain embodiments, handheld devices can include separate monitors or devices managed by the User 105. In some embodiments, the Sensor 110 measures analyte levels relatively continuously in real-time or near real-time, without user intervention. That is, the Sensor 110 can record and transmit measurements continuously or on defined intervals, without requiring the User 105 to manually initiate a recording. For example, the Sensor 110 can record the relevant data every second, every five seconds, every minute, every five minutes, and so on. In some embodiments, the Sensor 110 can operate in an on-demand configuration, where the User 105 manually triggers collecting of measurement data. This granularity enables the System 120 to perform more accurately during the data analysis phase.

In certain embodiments, the particular configuration of the Sensor 110 may depend in part on the type of ketone or other data being measured. For example, in certain embodiments, the Sensor 110 may be configured to measure acetoacetate levels in the user (e.g., via urinalysis). Acetoacetate is generally the first ketone produced during ketosis, and can be used by the body as an alternative energy source when glucose is unavailable or low. Acetoacetate is generally created during the breakdown of fatty acids, and can be used as energy (or may be converted or broken down into other ketones discussed below). In some embodiments, the Sensor 110 is configured to evaluate the urine of the user, in order to return a measurement of acetoacetate. For example, the Sensor 110 may include urinalysis strips. One advantage of such Sensors 110 is that they are affordable, readily available, and easy and non-invasive to use. However, the readings may be less accurate due at least in part to the simple fact that measuring acetoacetate requires urine, which is not always available. Thus, acetoacetate readings may fail to deliver rapid measurements in response to changing conditions.

In some embodiments, in addition to or instead of measuring acetoacetate, the Sensor 110 may be configured to measure acetone levels (e.g., via analysis of the user's breath). Acetones are small ketone bodies produced during ketosis. For example, as acetoacetate breaks down in the body, acetone may be produced. Acetone does not typically carry energy for the user, but is instead a byproduct of ketosis. Generally, acetone is diffused into the lungs of the user, and is exhaled during respiration. Thus, in one such embodiment, the Sensor 110 is configured to measure acetone levels in the breath of the user. For example, the user may blow into the Sensor 110 periodically. One advantage of such Sensors 110 is that they are non-invasive and simple to operate. However, by requiring the user to breathe into the Sensor 110, they may impose additional inconvenience and thereby reduce the efficacy of the system.

In some embodiments, the Sensor 110 is configured to measure beta-hydroxybutyrate levels. This may include, for example, performing blood analysis, analyzing interstitial fluid, and the like. Beta-hydroxybutyrate is a ketone which may be synthesized in the liver (e.g., converted from acetoacetate). Beta-hydroxybutyrate carries energy throughout the body (particularly when other carriers, such as glucose, are low or unavailable). In some embodiments, the beta-hydroxybutyrate measurements returned by the Sensor 110 are an accurate and responsive measurement due to the rapid nature with which beta-hydroxybutyrate levels change in humans. That is, by measuring beta-hydroxybutyrate levels, the Sensor 110 enables the system to rapidly detect and evaluate the changing conditions of the user (particularly in response to actions or therapies, such as medicinal or food intake), because the beta-hydroxybutyrate levels change rapidly. This is particularly true when the Sensor 110 is an implanted or wearable device that can collect real-time (or near real-time) samples for measurement. In certain embodiments, in addition to or instead of monitoring urine, breath, and/or blood, the system can also use a Sensor 110 to monitor analyte levels via sweat of the user.

In some embodiments, the Sensor 110 includes a glucose sensor that measures a concentration of glucose or a substance indicative of the concentration or presence of another analyte, such as ketones. In some embodiments, the glucose sensor is a continuous device, for example a subcutaneous, transdermal, transcutaneous, non-invasive, intraocular, intravascular, and/or intravenous device. In some embodiments, the device can analyze a plurality of intermittent blood samples. The glucose sensor can use any method of glucose measurement, including, but not limited to, enzymatic, chemical, physical, electrochemical, optical, optochemical, fluorescence-based, spectrophotometric, spectroscopic, optical absorption spectroscopic, Raman spectroscopic, polarimetric, calorimetric, iontophoretic, radiometric, and the like.

The glucose sensor can use any known detection method, including invasive, minimally invasive, and non-invasive sensing techniques, to provide a data stream indicative of the concentration of the analyte in a host. The data stream is typically a raw data signal that is used to provide a useful value of the analyte to a user, such as a patient or health care professional (HCP) who may be using the sensor. In certain embodiments, the healthcare professional can include, for example, a doctor, a physician, a nurse, a caregiver, and the like.

Although some examples herein are drawn to a glucose sensor that can measure the concentration of glucose in a host, the systems and methods of embodiments can be applied to any measurable analyte. It should be understood that the devices and methods described herein can be applied to any device that can detect a concentration of analyte and providing an output signal that represents the concentration of the analyte. For example, as discussed, in certain embodiments the Sensor 110 can measure ketones and/or lactate.

In some embodiments, the type of Sensor 110 may differ for measuring ketones. For example, the Sensor 110 may be configured to measure blood beta-hydroxybutyrate (beta-HBA) concentrations using an electrochemical oxidative hydrolysis sensor. In certain aspects, Sensor 110 measures nicotinamide adenine dinucleotide, reduced form, which is the reaction product of ketone 3-p-hydroxybutyrate (3HB) and NAD+(nicotinamide adenine dinucleotide, oxidized form) in the presence of enzyme 3-hydroxybutyrate dehydrogenase (3HBDH, EC 1.1.1.30).

In some embodiments, the analyte sensor is an implantable sensor, such as described with reference to U.S. Pat. No. 6,001,067 and U.S. Patent Publication No. US-2011-0027127-A1. In some embodiments, the analyte sensor is a transcutaneous sensor, such as described with reference to U.S. Patent Publication No. US-2006-0020187-A1. In yet other embodiments, the analyte sensor is a dual electrode analyte sensor, such as described with reference to U.S. Patent Publication No. US-2009-0137887-A1. In still other embodiments, the sensor is configured to be implanted in a host vessel or extracorporeally, such as is described in U.S. Patent Publication No. US-2007-0027385-A1. These patents and publications are incorporated herein by reference in their entirety.

In certain embodiments, the Sensor 110 can utilize a single working electrode sensor with analyte sensing capability to measure multiple analytes. Accordingly, in certain embodiments, Sensor 110 is configured to demux or demultiplex the multiple signals corresponding to measurements of the multiple analtyes using measurement electronics. In certain embodiments, the measurement electronics are configured to change potential (+/− voltage), impedance measurements, duty cycling, and the like to demux the multiple signals. In a related embodiment, a single working electrode can be duty cycled to measure individual analytes one at a time, each for an optimized duration of time. Such embodiments may require mediator selectivity.

In certain embodiments, the Sensor 110 includes an on skin reference electrode and one or more below skin working electrodes to measure multiple analytes. In certain embodiments, each of the one or more sensors has a membrane formed of a different chemical material or other configuration. Accordingly, in certain embodiments, each membrane is configured per analyte so the Sensor can better measure different analytes.

Sensor and Device Communication

In certain embodiments, the Sensor 110 is communicatively coupled with a Device 115 associated with the User 105. That is, the Sensor 110 transmits its measurements to the Device 115, as discussed. In certain embodiments, Device 115 includes a memory configured to store the measurements. For example, Device 115, stores both current and past measurements.

In certain embodiments, the Sensor 110 is wirelessly coupled to Device 115, such as using a traditional communication device, such as WiFi, Bluetooth, or the like.

In certain embodiments, the Sensor 110 is coupled to the Device 115 using a body area network (BAN). In certain embodiments, a BAN utilizes electro and/or chemical paths of the body by which to transfer data between devices coupled to the body. For example, in certain embodiments, the Sensor 110 includes one or more wires or electrodes coupled to the body and is configured to send electrical signals via the one or more wires or electrodes into the body. In certain embodiments, the electrical signals are modulated with data, such as information indicative of one or more analyte levels. The electrical signal travel through the body, using the body itself as a network, and are received by Device 115 coupled to the body via one or more wires or electrodes. For example, in certain embodiments, the Device 115 may be a smart device worn on the body, such as a smart watch. The Device 115, in certain embodiments, demodulates the received signal to extract the data.

In certain embodiments, the Device 115 and Sensor 110 form a body wireless mesh network that allows multiple devices to connect and communicate information reliably. For example, in certain aspects, the Device 115 couples with multiple Sensors 110 in a body wireless mesh network. In certain embodiments, additional devices, such as fitness trackers, smartwatches, and/or the like, such as described further herein, also join the body wireless mesh network to provide additional data and/or processing capability.

In certain embodiments, the body wireless mesh network is formed using a BAN. In certain embodiments, the body wireless mesh network is formed using Wifi, or Bluetooth, such as Bluetooth Low Energy (BLE). In certain embodiments, the body wireless mesh network is formed using one or more communication protocols, such as to optimize performance and/or battery life. For example, in certain embodiments, a Sensor 110 includes a low power processor and uses a BAN for communication. In certain embodiments, a Sensor 110 uses a medium power processor and both a BAN and BLE for communication. In certain embodiments, a Sensor 110 or another device uses a high power processor and both a BAN and BLE for communication. In certain embodiments, as discussed, the processing of data can occur on one or more devices other than Device 115. In certain embodiments, the processing is performed by one or more devices in the body wireless mesh network. In certain embodiments, the processing location and communication protocol used are to optimize performance. In certain embodiments, the processing location and communication protocol used are to optimize battery life. In certain embodiments, the processing location is distributed among multiple devices.

Device Data Collection

In certain embodiments, the Device 115 can consider a variety of other data for analysis and/or evaluation. This can include one or more of the physical state, mental state, and/or activities of the User 105. The physical state can include, for example, one or more of the weight, a disease state, an insulin resistance or sensitivity, a glucose sensitivity, a heart rate of the User 105, and the like.

In some embodiments, the user's mental state generally includes the emotional and mental response of the User 105. This can include, for example, one or more of whether the User 105 feels annoyed, content, anxious, focused, and the like. In certain embodiments, the mental state includes the level of hunger the user is experiencing.

In some embodiments, the additional data can be collected in one or more ways. In certain embodiments, some or all of the information can be provided as user input. For example, in certain embodiments, the User 105 may use the Device 115 to indicate one or more of physical state or mental state. In certain embodiments, the User 105 utilizes a graphical user interface (GUI) on Device 115 to provide the indication(s). In some embodiments, the User 105 can specify one or more activities, such as physical exercise, that they have recently taken place or are currently taking place, food that has been eaten or is currently being eaten, or the like.

In certain embodiments, some or all of the additional data is collected using one or more other devices that provide the data to Device 115. For example, the one or more other devices may couple to Device 115 similar to how Sensor 110 couples to Device 115. For example, the heart rate of the User 105 may be determined using a heart rate monitor. In certain embodiments, one or more activity or fitness trackers are used to collect a portion of the additional data. In certain embodiments, the activity or fitness trackers can include smart watches and similar devices. In some embodiments, the actions of the user, such as physical exercise, are similarly identified by activity or fitness trackers.

In some embodiments, the additional data can be correlated with the one or more analyte measurements based on time. For example, the mental state, physical state, and/or actions can be timestamped based on when they occurred, such that the Device 115 can associate the analyte measurements of the User 105 at any given time with the corresponding mental state and/or physical state that the user was experiencing. Similarly, the Device 115 can associate the analyte measurements with activities or actions the user was engaging in at the time.

Pattern Generation

In certain embodiments, the one or more Patterns 125 are generated based on the collected user data. In certain embodiments, the user data includes the one or more measurements of analyte levels from the Sensor 110. In certain embodiments, the user data includes the additional data received by Device 115. In certain embodiments, the one or more Patterns 125 include a Pattern 125 indicative of an analyte level of the User 105. In certain embodiments, the one or more Patterns 125 include a Pattern 125 indicative of a physical state of the User 105. In certain embodiments, the one or more Patterns 125 include a Pattern 125 indicative of a mental state of the User 105. In certain embodiments, the Patterns 125 include a Pattern 125 to monitor glucose and ketone levels of the user to predict diabetic ketoacidosis (DKA). In related embodiments, the Patterns 125 may also be used to monitor lactate or hydration markers (such as potassium or sodium), other biomarkers (e.g., heart rate variability, temperature changes, blood pressure changes, etc.) and the like.

In certain embodiments, a Pattern 125 indicative of an analyte level of the User 105 is generated based on the one or more measurements of analyte levels from the Sensor 110. In certain embodiments, a Pattern 125 indicative of a physical state of the User 105 is generated based on additional data relating to physical state of the User 105. In certain embodiments, a Pattern 125 indicative of a mental state of the User 105 is generated based on additional data relating to mental state of the User 105.

Figure 3:
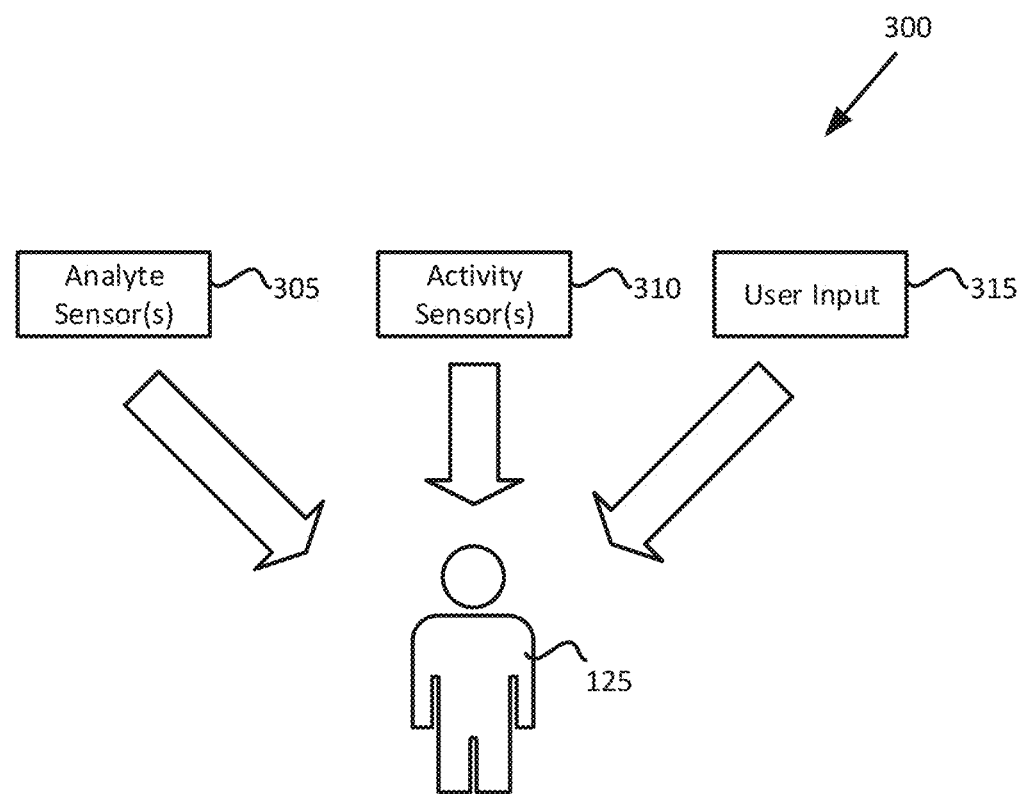
FIG. 3 depicts a workflow for building one or more patterns, according to certain embodiments disclosed herein.

FIG. 3 depicts a workflow 300 for building one or more Patterns 125, according to certain embodiments disclosed herein. The illustrated workflow 300 depicts a number of inputs used to generate one or more Patterns 125. In particular, as discussed, and as shown in FIG. 3, the number of inputs can include one or more of measurements of one or more analyte levels from one or more analyte sensors 305 such as Sensor 110. In certain embodiments, the number of inputs can include one or more of measurements of activities or other physical states from one or more activity sensors 310. In certain embodiments, the number of inputs can include one or more user inputs 315 of physical state or mental state, such as from Device 115. In certain embodiments, one type of input, such as analyte level, physical state, user activity, or mental state, is used to generate one Pattern 125. In certain embodiments, multiple types of input are used to generate one Pattern 125.

Although several inputs are depicted, in some embodiments, any input may be provided separately. For example, at a given time, the analyte levels of the user may be available as input, but the mental state of the user may be unknown. For example, in some embodiments, the mental state can be unknown because the user has not provided any response or input indicating their mental state. In certain embodiments, the system can nevertheless utilize the Pattern 125 to evaluate the available input, even in the absence of some other inputs.

As discussed above, a Pattern 125 can include one or more of data models, rate of change, trend lines, patterns and trends, correlations, trained machine learning (ML) models, and the like. Generally, a Pattern 125 is used to represent user-specific data, based on the provided inputs. For example, in certain aspects, a Pattern 125 represents past, current, and future predicted values. In certain aspects, a Pattern 135 indicates future predicted values, such as based on past and current values. Depending on the Pattern 125, in certain embodiments, the values may be one or more of analyte levels, physical state, or mental state.

In some embodiments, a Pattern 125 is a personalized pattern that is built based on data related to an individual user. In certain embodiments, a Pattern 125 is a demographic-specific pattern, rather than a personalized pattern. For example, data from multiple users having a particular demographic is correlated to generate a pattern. A demographic may be based on users having similar one or more of age, gender, ethnicity, activity levels, or the like. In some embodiments, the Pattern 125 is built based on user-specific body needs, including differentiation based on demographics of the user. By using this user-specific data, in some embodiments, the system can build an optimized and personalized path and compare user-specific data with overall results and/or individual goals of the user. Further, in at least one embodiment, the Pattern 125 is generic and can be used for any individual user. In some embodiments, the Pattern 125 is built using a combination of both user-specific data, as well as demographic-specific or other general data.

In certain embodiments, the input is used to build and update the one or more Patterns 125. For example, in certain embodiments, the Device 115 determines rate of change (ROC) between past values and current values to predict future values. In certain embodiments, the Device 115 generates the one or more Patterns 125 using one or more of computer modeling, machine learning, pattern identification, a bolus calculator, a function, or an algorithm.

In certain embodiments, the one or more Patterns 125 can be generated or updated using real-time or nearly real-time data to classify and predict user states. Accordingly, a user may not need to log meals or count calories to predict their own state and progress.

Figure 4:
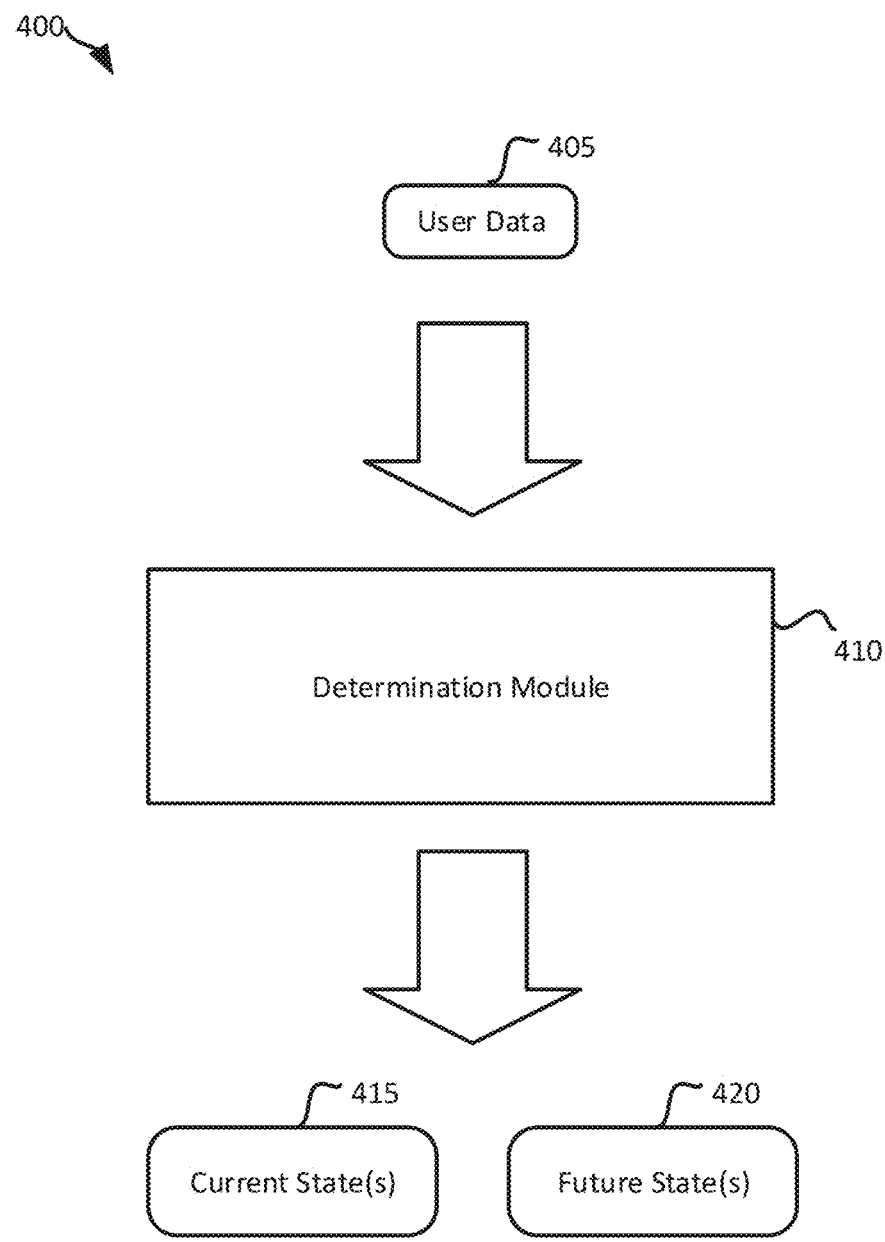
FIG. 4 depicts a workflow for determining current and future user states based on user data, according to certain embodiments disclosed herein.

FIG. 4 depicts a workflow 400 for determining current and future user states that form one or more Patterns 125 based on user data, according to certain embodiments disclosed herein. As illustrated, User Data 405 is provided to a Determination Module 410 to generate one or more Current State(s) 415 and one or more Future State(s) 420, which may correspond to one or more Patterns 125. Generally, the User Data 405 can include any data relating to a user, and the Current States 415 and Future States 420 can correspond to any analyte level, mental, and/or physical state.

In certain embodiments, the User Data 405 can include current data associated with the user, as discussed. In certain embodiments, the User Data 405 includes current analyte measurements. In certain embodiments, the User Data 405 includes mental characteristics of the user. In certain embodiments, the User Data 405 includes recent activity of the user. In certain embodiments, the recent activity includes physical activities that the user engaged in within a predefined period of time. In certain embodiments, the User Data 405 includes current activities of the user. In certain embodiments, the User Data 405 includes planned future activities of the user.

In certain embodiments, the Determination Module 410 utilizes past data that corresponds to the user. In some embodiments, one or more Patterns 125 include a trained machine learning model. Accordingly, in some embodiments, Determination Module 410 can iteratively train the one or more Patterns 125 using user data to receive current user data as input, and output estimated or predicted future state as output. In certain embodiments, the Determination Module 410 includes one or more of computer modeling, machine learning, pattern identification, a bolus calculator, a function, or an algorithm that receive user data as input, and return predicted states. In certain embodiments, the Determination Module 410 updates one or more Patterns 125 and/or correlations built on prior data.

Based on this analysis, the Determination Module 410 can return Current State 415, and/or a Future State 420. Both the Current State 415 and Future State 420 can include a variety of elements, including one or more of analyte levels, physical states of the user, mental states of the user, and the like.

In certain embodiments, the Future States 420 can include a predicted level of hunger. In certain embodiments, the Future States 420 include whether the user will feel irritable or attentive, or any other emotion or state that the user wishes to predict or consider. In at least one embodiment, the Future States 420 are associated with a timeline, delay, latency, or other indicator of when the state is expected to begin. In certain embodiments, the Future States 420 include an indication as to how long the state will last. This can be learned from prior data collection. In certain embodiments, the delay is learned based on the user's previous trends and patterns.

As an example, in certain embodiments, a Pattern 125 may be generated and used to predict whether the user will enter diabetic ketoacidosis (DKA), as well as the urgency or delay before DKA is entered. For example, based on a Pattern 125 and the current User Data 405 (e.g., glucose and/or ketone levels) and/or Current State 415, the Determination Module 410 may determine that the Future States 420 include DKA, with onset of the state beginning in about one hour. In various embodiments, the Pattern(s) 125 used to predict DKA can also be based on a wide variety of other elements, such as, by way of example, hydration levels (e.g., detected via measurements of potassium, sodium, or others), detection of early markers of infection (e.g., heart rate variability (HRV), lactate levels, temperature changes, and the like), as well as other elements such as changes in blood pressure and/or heart rate.

If caught sufficiently early, DKA may be reversible using aggressive hydration (to flush out the ketones), insulin treatments, or a combination. However, if not detected early, DKA generally requires immediate hospitalization. In an embodiment, therefore, the Future State 420 indicates the estimated latency until the onset of DKA in order to allow the user to quickly respond appropriately. Based on this latency, the system may take a number of actions such as instructing the participant on how to respond, contacting a clinician, and the like.

In some embodiments, the Patterns 125 can be used to identify and/or predict Future States 420 on a granular level. In certain embodiments, the system can predict whether the user is in or will enter ketoacidosis, as well as a particular type of ketoacidosis. For example, the system may identify patterns of ketone and/or glucose levels for the user that lead to the user entering specific types of ketoacidosis. These types can include, for example, hyperglycemic ketoacidosis, euglycemic ketoacidosis, diet-based ketoacidosis, and the like. In certain embodiments, therefore, the Patterns 125 can be used to identify specific trends and measurements that lead to specific types of concerns or issues. This can allow the user to not only determine the specific concerns relevant to them, but also how to avoid them.

Such embodiments may be particularly useful when users exhibit non-typical characteristics, such as with respect to medications they consume. For example, SGLT2 class drugs can have differing effects on the user depending on whether the user has type 2 or type 1 diabetes. While users with type 2 diabetes can consume SGLT2 class drugs with no or with minimal concern, those with type 1 diabetes who consume SGLT2 class drugs can build up ketones in their blood even when they are not hyperglycemic. This can cause such users to enter diabetic ketoacidosis (DKA). To remedy these concerns, some embodiments of the present disclosure monitor both glucose and ketone levels to determine the cause and type of ketoacidosis, which improves patient results.

In certain embodiments, these Patterns 125 can similarly be used to improve treatment of concerns such as ketoacidosis. For example, when a user enters diabetic ketoacidosis, typical treatments include lowering the user's glucose levels as quickly as possible. This can include utilizing insulin to lower the user's glucose levels and clear ketones from the user's blood. For example, ketosis and ketonuria reflect a greater degree of insulin deficiency than hyperglycaemia alone. The presence of ketones may indicate that insulin concentrations are too low not only to control blood glucose concentrations, but also to prevent the breakdown of fat (lipolysis). In particular, high ketones in the blood are associated with high levels of fatty acids and together create insulin resistance. A user with significant ketonaemia may require more insulin than usual to control the blood glucose. Thus, utilizing insulin to lower the user's glucose levels and clear ketones from the user's blood is especially important in such situations.

In certain embodiments, therefore, Patterns 125 configured to identify connections between glucose, ketones, and/or insulin can be used to better identify and/or treat users entering diabetic ketoacidosis. For example, the system may interface with an insulin pump configured to provide insulin to the user. In some embodiments, the system can automatically determine and administer appropriate amounts of insulin based on ketone and glucose levels. In some embodiments, the system may provide an indication to the user of an appropriate amount of insulin to administer based on ketone and glucose levels indicating diabetic ketoacidosis.

In some embodiments, if the predicted Future State 420 is sufficiently far into the future (e.g., above a defined threshold, which may be user-specific and/or learned based on prior data), the system can take such interventions as facilitating or initiating insulin administration. In at least one embodiment, other approaches (such as hydration) can be suggested. For example, the system may alert the user and advise them to hydrate as much as possible. In some embodiments, the system may direct the user to ingest a prescribed amount of hydration (e.g., two liters of water). This amount may be determined, for example, based on clinical input or direction of a healthcare provider.

In contrast, if the predicted onset of DKA is more imminent, the system may instead urge or alert the user to immediately go to the hospital or emergency room, as there is not enough time to reverse it at home. In at least one embodiment, the system may further facilitate this assistance, such as by alerting and/or connecting a remote team of healthcare provider(s) to monitor the user, arranging transportation to the hospital, and the like.

As another example, ketosis has been shown to be beneficial for treating epilepsy and/or migraines in some patients. In some embodiments, in addition to or instead of predicting the presence of ketosis as a Future State 420, the Determination Module 410 can predict whether the patient's epilepsy, migraines, or other condition will remain controlled. In some aspects, effective ketosis management (with the aid of the systems described herein) may allow for the reduction or elimination of other traditional treatments (such as medication) for epilepsy, migraines, and other conditions. In some patients, such as those with refractory epilepsy who do not respond well to anti-epileptic or anti-seizure drugs, their condition may be entirely controlled using nutritional ketosis. That is, ketosis can be used as a replacement primary therapy, independent of medication therapies.

As still another example, ketosis may be beneficial for cancer treatments. For example, there is evidence that ketones can help to slow or stop tumor growth in some cases. Subsequent treatment (e.g., with chemotherapy) may therefore require lower doses, resulting in fewer negative side effects. In some aspects, therefore, the system can predict Future States 420 regarding such cancer states in order to aid treatment. In at least one embodiment, in addition to or instead of simply maintaining ketosis, the system assists the user in maintaining specific ketone levels (e.g., 0.5 mmol/L to 1.5 mmol/L), which may help achieve the optimal effect (especially in combination with other treatments such as chemotherapy) to improve treatment outcomes.

Improving Patterns

In certain embodiments, to help generate improved one or more Patterns 125, the Device 115 may suggest to the user to evaluate one or more of test meals, supplements, and activities. For example, the Device 115 may record a current state of the user. The Device 115 may then indicate one or more of a food, supplement, or activity to be tested by the user, and subsequently record the resulting state of the user after the test is completed by the user. Accordingly, the Device 115, based on the resulting state, can predict how a similar food, supplement, or activity can affect the user in the future. In certain embodiments, Device 115 utilizes such information when generating Patterns 125 as discussed, to better predict user state based on one or more actions indicated as performed by the user. This can allow the decision support system to more rapidly improve the patterns based on concrete real-world data, rather than simply passively collecting data.

For example, in certain embodiments, by utilizing such tests, the system can determine the efficacy and dosage for supplements. In certain embodiments, the supplements are ketone diet supplements. That is, by instructing the user to consume the supplement(s) at a specified time and subsequently analyzing the user's analytes, the system can learn whether the supplements help keep the user in ketosis or help the user reach ketosis. Similarly, the system can learn the optimal dosage, optimal dosage timing, and the like, based on observing how the user's body reacts to the test dosage and time.

Patterns as User Trend Lines

In certain embodiments, a Pattern 125 includes data relating to one or more trends in one or more analytes of the user. Patterns as user trend lines will be described with reference to FIG. 5.

Figure 5:
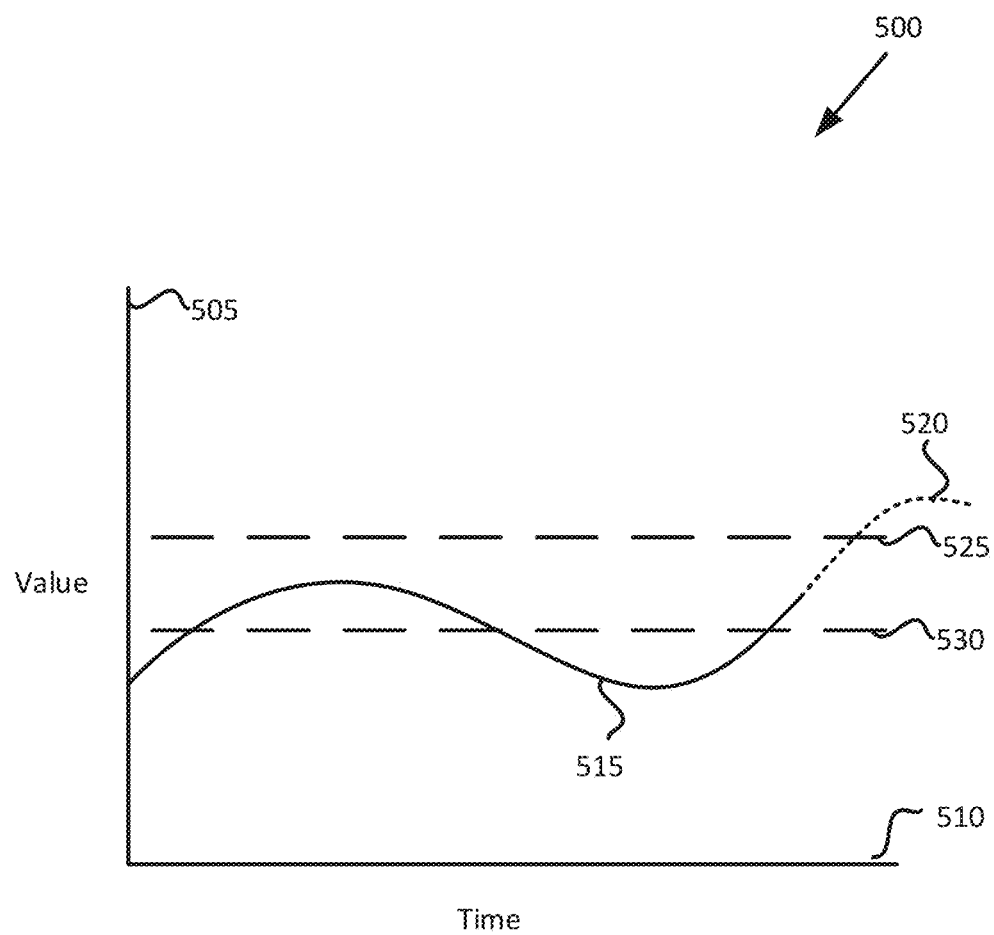
FIG. 5 illustrates a user trend line generated based on user data, according to certain embodiments disclosed herein.

FIG. 5 illustrates a user trend line generated based on user data, according to certain embodiments disclosed herein. In the illustrated plot, the value for one or more analytes is depicted on the Vertical Axis 505, as a function of time (plotted on the Horizontal Axis 510). In some embodiments, the trend line depicts a Pattern 125 learned over time, based on user data. In the illustrated embodiment, the solid portion of the line (marked 515) indicates actual analyte measurements for the user, while the dotted portion (marked 520) indicates estimated or predicted values for the analyte. Further, in certain embodiments, the dashed horizontal lines (marked 525 and 530) indicate an optimal range for the analyte.

In certain embodiments, the optimal range is a range of ketone levels or analyte levels correlated with ketone levels correlated with ketosis. For example, a ketosis state may be defined as having a ketone concentration between approximately 0.5 millimolars per liter (mmol/L) and 3.0 mmol/L in blood of the user.

In certain embodiments, the optimal range can be determined in any number of ways. In certain embodiments, the user specifies the range based on their own preferences. In some embodiments, the range is determined by the Device 115 based on the user's demographics. For example, the Device 115 can refer to scientific literature and/or studies to determine an ideal range for the user, based on the user's demographics. In certain embodiments, the optimal range for a female user may differ from the optimal range for a male user, as indicated in the scientific literature. The Device 115 can therefore set the range that is best suited for the user's demographics.

In certain embodiments, the Device 115 identifies an optimal range based on goals specified by the user. For example, the optimal range of a particular analyte may differ depending on whether or not the user wishes to lose weight. Once the user provides their targets or goals, the Device 115 can evaluate scientific literature to determine the optimal range(s) for the user to achieve these goals.

In certain embodiments, the Device 115 tracks the value of the analyte over time, and generates the trend line using this data. As illustrated, the analyte measurement for the user was initially below the optimal range, and raised into the optimal range over a period of time. The level then dropped outside of the optimal range again, before beginning to rise again into the optimal range. In embodiments, these changes can be due to a variety of inputs as discussed, such as activity of the user, meals consumed, and the like. In certain embodiments, in addition to monitoring the analytes, the Device 115 monitors activities of the user in order to correlate the user's actions with the shifting analytes.

For example, the Device 115 may record times when the user eats, as well as the particular meals consumed. This can include the calories consumed, the particular food that was consumed, and the like. In some embodiments, the monitored activities include physical actions of the user, such as exercise. By mapping these actions and activities against the determined trend in the analyte values, the Device 115 can generate one or more Patterns 125 and correlations, and learn how certain activities and actions will influence the analyte levels. Using these patterns, therefore, the Device 115 can predict how current and planned actions will influence the analyte.

In the illustrated embodiment, based on the generated one or more Patterns 125, the Device 115 estimates that the analyte level will continue to rise until it is outside of the optimal range, before leveling off. In certain embodiments, the Device 115 makes this prediction based on the current analyte level(s) for one or more analytes, as well as the current trend(s). For example, because the analyte level is currently increasing, the Device 115 can infer that it will continue to do so. In at least one embodiment, the prediction is based in part on a rate of change for the analyte. For example, the Device 115 can infer that the analyte will continue to change at roughly the same rate that it is currently changing, at least for some period of time.

In some embodiments, the Device 115 predicts the future measurements based on the user's prior patterns. For example, if the Device 115 knows that the user consumed a certain meal at a specific time, the Device 115 can analyze the subsequent changes in analytes, as reflected by the trend line, in order to learn how the specific meal affected the user's analytes. If the Device 115 learns that the user recently consumed a similar or identical meal, the trend line can thereby be used to predict how much the analytes will change, based at least in part on how much the analytes previously changed. In certain embodiments, the Device 115 similarly evaluates planned actions in determining the predicted levels. For example, the user may indicate that they plan to engage in physical activity later, or that they plan to consume a meal later. Based on these actions and the previously-generated pattern(s), the Device 115 can predict how the analyte levels will change in response.

Continuous Pattern Updates

In certain embodiments, the Device 115 can iteratively and continuously update and revise one or more Patterns 125 for the user, in order to ensure future predictions remain accurate. Continuous pattern updates will be described with reference to FIG. 6.

Figure 6:
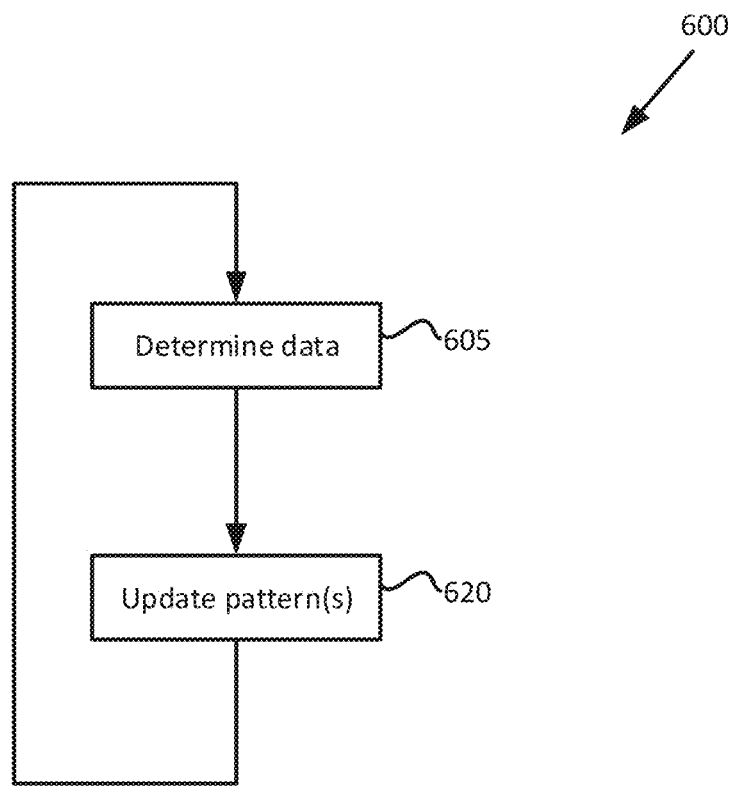
FIG. 6 is a flow diagram illustrating a method for building and refining patterns to aid users, according to certain embodiments disclosed herein.

FIG. 6 is a flow diagram illustrating a method for building and refining one or more Patterns 125 to aid users, according to certain embodiments disclosed herein. The method 600 begins at block 605, where a Device 115 determines data for a user. As discussed above, this can include receiving data from one or more sensors, requesting or collecting data from the user directly, and the like.

In at least one embodiment, the Device 115 determines the mental state of a user as data by pushing a survey or request to the user, requesting that the user indicate their mood, hunger, and the like. In certain embodiments, the Device 115 collects this data by waiting for the user to provide it, with or without a survey. In certain embodiments, Device 115 determines actions that the user has recently engaged in or is currently engaging in as data. In certain embodiments an action is considered "recent" if it occurred within a predefined period of time. In some embodiments, the action is sufficiently recent for consideration if it occurred after the last time data was collected. For example, suppose the user performed a first action at 1:00 pm, the Device 115 collected and evaluated data at 1:05 pm, the user then performed a second action at 1:10 pm, and the Device 115 collected and evaluated data again at 1:15 pm. In such certain embodiments, the first action is considered "recent" or associated with the data collected at 1:05 pm, but is not considered recent or relevant to the data collected a 1:15.

The method 600 then continues to block 620, where the Device 115 generates, builds, trains, updates, and/or refines one or more Patterns 125 based on the collected data. In some embodiments, the Device 115 does so by updating the one or more Patterns 125 to reflect the currently-received data. This includes adding any measurements to current trends and values, adding an indication of activities undertaken at the appropriate points in the trend, and the like. This allows the Device 115 to continuously update the one or more Patterns 125, such that subsequent evaluations are improved.

In certain embodiments, if the one or more Patterns 125 includes an ML model, the Device 115 updates the model by labeling one or more prior records with the current state of the user, indicating a latency or delay between the original data collection and the current state. The Device 115 can then use these labeled records to refine the model, such that the data models are able to better predict not only the future state of the user, but also the time at which that future state will occur. In the illustrated embodiment, this method 600 then repeats. This allows the Device 115 to continuously monitor the user's status to provide updates, as well as to constantly refine the one or more Patterns 125.

Pattern Correlation

In certain embodiments, once one or more Patterns 125 have been generated for use, the Device 115 can correlate the one or more Patterns 125 with one or more targets associated with the user. Pattern correlation will be described with reference to FIG. 7.

Figure 7:
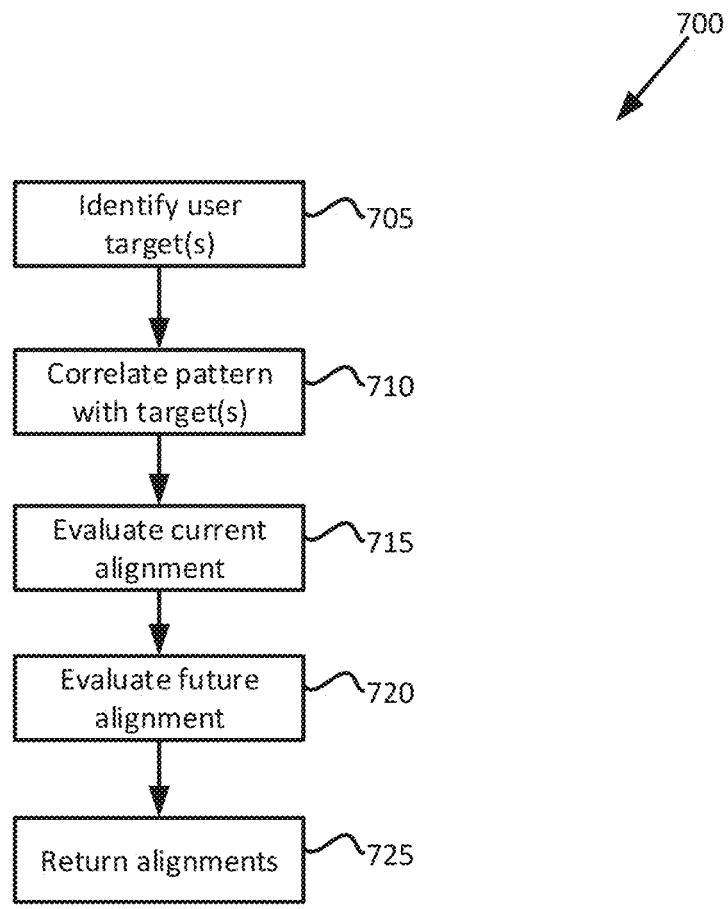
FIG. 7 is a flow diagram illustrating a method for correlating user patterns with user targets to determine alignment, according to certain embodiments disclosed herein.

FIG. 7 is a flow diagram illustrating a method 700 for correlating one or more Patterns 125 with user targets to determine alignment, according to certain embodiments disclosed herein. Note that the blocks of the method 700 may not necessarily be performed in the order described herein. Furthermore, some blocks or states herein may be omitted, and/or additional blocks or states may be added.

The method 700 begins at block 705, where a Device 115 identifies one or more targets associated with the user. In certain embodiments, the user targets generally indicate goals or desires for the user. For example, the user targets may indicate one or more of a desired analyte level, mental state, or physical state. For example, without limitation, the targets can include one or more of weight loss, mental health, glucose sensitivity, glucose level, insulin resistance or sensitivity, to achieve ketosis, and the like. In some embodiments, the targets can indicate a desired magnitude or value. For example, a target may indicate a desired ketone range for achieving ketosis in certain embodiments. Further, in certain embodiments, a target may indicate one or more of a desired weight, a desired level of insulin resistance or sensitivity, and the like. The method 700 then continues to block 710, where the Device 115 correlates the previously-generated one or more Patterns 125 with the user's targets.

In some embodiments, there is a direct correlation between one or more Patterns 125 and a target. For example, if a Pattern 125 indicates an analyte level of a user over time, and the target is a particular analyte level, the correlation may simply be whether the one or more Patterns 125 indicates the analyte level satisfies or aligns with the target. For example, the Device 115 in certain embodiments correlates whether the one or more Patterns 125 indicate the target is currently achieved. In another example, in certain embodiments, Device 115 correlates whether the one or more Patterns 125 indicate a target will be achieved at a future time. In certain aspects, the correlations may simply be whether the one or more Patterns 125 indicate that a mental state and/or physical state satisfies or aligns with the target.

In some embodiments, correlating the one or more Patterns 125 with the one or more targets includes identifying overlap or alignment between the one or more Patterns 125, and in certain embodiments additional data, and the one or more targets. In certain embodiments, the data represented by one or more Patterns 125 and/or other data input in Device 115 are interrelated. For example, in certain embodiments, the values and/or trends in one Pattern 125 affects another. Additionally, in certain embodiments, the one or more Patterns 125 depend in part on the activities and consumption of the user. Thus, in certain embodiments, correlating the one or more Patterns 125 against the targets can involve evaluating a number of dimensions to identify likely effects and mismatches between the desired states and the actual states.

In some embodiments, as discussed, during data collection, additional data can be correlated with the one or more analyte measurements based on time. For example, the mental state, physical state, and/or actions can be time-stamped based on when they occurred, such that the Device 115 can associate the analyte measurements of the User 105 at any given time with the corresponding mental state and/or physical state that the user was experiencing. Accordingly, in certain embodiments, correlating the one or more Patterns 125 and targets may include determining whether a particular analyte level or ROC of an analyte level is correlated with a particular mental state and/or physical state based on the data collection. In certain embodiments, correlating the one or more Patterns 125 and targets may include determining whether a particular analyte level or ROC of an analyte level is correlated with a particular mental state and/or physical state based on demographic data of the user. In certain embodiments, correlating the one or more Patterns 125 and targets may include determining whether a particular analyte level or ROC of an analyte level is correlated with a particular mental state and/or physical state based on general population data. In some such embodiments, the correlated mental state and/or physical state may be correlated with one or more targets.

In certain embodiments, correlating the one or more Patterns 125 and targets includes determining alignment between them. In certain embodiments, this alignment can include physical state and/or mental state, as well as a combination. In certain embodiments, determining the alignment of combinations of physical and mental state can include, for example, correlations between mental and physical states.

In some embodiments, multiple targets can be defined. In at least one embodiment, each target can be associated with a weight or importance, such that the Device 115 can identify the most important targets, and adjust or weight the alignments accordingly. In certain embodiments, evaluating the alignment includes generating a value representing the alignment. This can include one or more binary values indicating whether the state(s) and target(s) are aligned. In some embodiments, the value also includes value(s) indicating the magnitude of any differences between the target and the state.

At block 715, the Device 115 evaluates the current state alignment. That is, the Device 115 determines whether the user's current state aligns with the target state(s). In certain embodiments, this alignment includes comparing the determined current mental state with the desired or target mental state. For example, the user may indicate a preference to minimize hunger. In some embodiments, the alignment can also include comparing the determined current physical state(s) of the user with the target physical state(s). For example, if ketosis is the goal, the Device 115 can determine whether the user is currently in ketosis. If the user has defined a minimum preferred level of insulin, the Device 115 can determine whether the user's current levels satisfy this threshold. In embodiments, this evaluation can include any number of comparisons, and is often far more complex.

In certain embodiments, the user can define targets that require correlations and comparisons across multiple states. This may require correlating between individual Pattern(s) 125. In certain embodiments, correlating between multiple Patterns 125 includes correlating between a mental pattern relating to the user's mental state and a physical pattern relating to the user's physical state. As an example of such a compound target, in some embodiments, the user may specify that they wish to maintain ketosis, unless their hunger level exceeds a threshold. In evaluating the current alignment, therefore, the system may correlate not only the physical patterns(s) to determine whether the user is in ketosis, but also the mental patterns to determine whether the hunger level exceeds the threshold. In certain embodiments, the Device 115 generates a first value or set of values indicating the current alignment.

As another example, there is some evidence that pregnancy may impact ketosis. For example, in some cases, pregnancy can be conceptualized as an accelerated and prolonged state of ketosis. There is evidence to suggest that ketone presence may negatively affect brain development of growing fetuses, which would imply that low or no ketone presence is desirable. Additionally or alternatively, if ketones are present in a pregnant user, the system may infer that the user is not consuming a sufficient quantity of carbohydrates, which are important for proper development. In some aspects, therefore, the alignment evaluation can ensure that the user (if pregnant) is not in ketosis or will not enter ketosis.

At block 720, the Device 115 evaluates the future alignment between the user's predicted states and the desired states. As above, in certain embodiments, this can include consideration of mental states, physical states, as well as a combination. For example, if the user wishes to maintain ketosis for as long as possible, the system can determine whether the current and future states are expected to maintain ketosis. As another example, if one target is to lose weight, the Device 115 can determine whether the current and/or future states are predicted to lead to weight loss. In some embodiments, such a determination may require cross-correlation between patterns/states. For example, the system may correlate the current and/or future states with weight loss models, such as Pattern(s) 125 generated for the user to predict weight loss, to determine whether the states are aligned. In certain embodiments, the Device 115 generates a second value or set of values indicating the future alignment.

In certain embodiments, the Device 115 can perform any number and variety of correlations, including cross-correlations between patterns/states, to determine the alignments.

At block 725, the system then returns the determined alignment(s). For example, if the analysis is performed in the cloud, the system can transmit an indication of the alignments to the Device 115.

Results Generation

In certain embodiments, the Device 115 uses combinations of the above-discussed evaluations to generate results or response for the User 105. In at least one embodiment, this includes outputting an indication of the alignment(s) to the user, such as via a GUI on the Device 115. Other example outputs can include using audio outputs, vibrations, and the like.

In certain embodiments, the Device 115 generates an output as to whether the one or more Pattern(s) 125 indicate that current and/or future state align or not with the one or more targets. For example, in certain embodiments, the Device 115 indicates whether the user is currently in ketosis or not. In certain embodiments, the Device 115 indicates whether the user will remain in ketosis or not.

In certain embodiments, the Device 115, using the data collected, is configured to provide robust feedback and results to a user that is user specific. For example, such feedback and results may not be possible without the described System 120.

In particular, in certain embodiments, the Device 115 is configured to utilize one or more Patterns 125 and additional data collected to make connections and correlations between different user states as discussed. The Device 115 may present the information indicating the connections and correlations to the user, in certain embodiments, so the user can make informed decisions. In certain embodiments, the Device 115 itself provides recommendations to the user for how to achieve their targets or goals. Such information may help provide accountability to a user maintaining a ketogenic lifestyle and reduce the need for coaching as the information allows self-empowerment of the user to make better decisions based on better information to maintain ketosis.

Ketone to User State Information

In certain embodiments, Device 115 provides information indicating correlations between analyte levels indicative of ketone levels and user state. For example, Device 115 provides information that correlates mental state of the user to ketone levels. In certain embodiments, the Device 115 correlates absolute ketone levels to mental state. In certain embodiments, the Device 115 correlates trends or rates of change in ketone levels to mental state. Accordingly, a user can use such information to determine how their ketone levels may affect their mental state.

In certain embodiments, Device 115 provides information that correlates physical state of the user to ketone levels. In certain embodiments, the Device 115 correlates absolute ketone levels to physical state. In certain embodiments, the Device 115 correlates trends or rates of change in ketone levels to physical state. Accordingly, a user can use such information to determine how their ketone levels may affect their physical state.

In certain embodiments, Device 115 provides information that correlates hunger levels of the user to ketone levels. In certain embodiments, the Device 115 correlates absolute ketone levels to hunger levels ate. In certain embodiments, the Device 115 correlates trends or rates of change in ketone levels to hunger levels. Accordingly, a user can use such information to determine how their ketone levels may affect their hunger levels.

Such information may be useful to a user in that the user can have knowledge of how ketone levels affect their body.

Such information may also be helpful in developing and making recommendation to a user, as discussed herein.

Impact Reports

In certain embodiments, as discussed, Device 115 can provide impact reports indicating how user actions, such as meals eaten or activities performed, affect one or more user states. For example, based on the data, one or more impact reports can be generated that indicate how one or more actions affected one or more of weight, insulin sensitivity, ketone level, or time the user was in ketosis. Accordingly, a user can use this information to make better informed decisions as to what actions to take to try and meet user targets.

Meal Information

Device 115 can provide correlations between meals consumed by a user and states of the user. In particular, as discussed, an important part of a ketogenic diet is what foods that a user consumes as this affects ketone levels. Equipped with such information, the user can make better informed decisions of what to eat, what not to eat, when to eat, and when not to eat, so as to achieve desired goals.

In certain aspects, Device 115 can indicate simulations and/or projections of how different meals will affect a user. For example, a user can determine exactly how eating a particular meal will affect the user, such as whether the meal will move the user out of ketosis. In certain embodiments, the simulations and/or projections can indicate, for example, that a particular meal is safe to eat, which the user was unsure of, such as allowing the user to safely eat a small amount of carbs while staying in ketosis.

In some embodiments, using the above-discussed patterns and correlations, the Device 115 can assist the user in learning and understanding not only which foods they can or should consume, but also which foods they should avoid. In many cases, a ketogenic diet (and therefore, the Device 115) can suggest a number of counterintuitive restrictions and recommendations. For example, many ketogenic regimens include a relatively high amount of fat for caloric content, which counterintuitively leads to significant fat and weight loss. Similarly, the regimen can include significant reduction in carbohydrates, which excludes traditional core calorie-providing foods. By consistently suggesting certain meals and/or consistently advising the user refrain from other meals, the Device 115 can help the user learn to avoid the problematic options. Eventually, the user may not need to rely on the Device 115 at all in order to know that a given meal is not acceptable.

In certain embodiments, as discussed, Device 115 can provide correlations between activities performed by a user and states of the user. In particular, as discussed, an important part of a ketogenic diet is what activities a user performs as this affects ketone levels. Equipped with such information, the user can make better informed decisions of what to do, what not to do, when to do something, and when not to do something, so as to achieve desired goals.

In some embodiments, the decision support system can be used to determine optimal or preferred days and/or times to consume foods or beverages that are ordinarily excluded from the user's diet. In certain embodiments, these times and days are often referred to colloquially as cheat days and cheat times. For example, the user may specify upcoming events or the decision support system can include records of predefined specific events such as birthday parties, vacations, special occasions, and the like. In certain embodiments, the decision support system can guide the user on how to optimally cheat. This can include instructing the user to modify their activity before and/or after the event to ensure that the "cheat" does not disrupt their progress. In a related embodiment, the decision support system can similarly suggest optimal times to increase intake of carbohydrates or other substances to prepare for planned physical activity or exertion.

In this way, the user can make more informed decisions regarding what foods to consume (if any), and what actions to take. For example, if the system assures the user that their current hunger is expected to pass in the next thirty minutes, the user may decide to refrain from eating in order to maintain ketosis. However, if the model indicates that the hunger is expected to persist or worsen, or that other issues may arise, such as increased irritability, the user may decide to break their ketosis and consume food.

Alarms

In certain embodiments, the Device 115 can generate alarms for various reasons. In some embodiments, any current mismatch between user state and desired state causes the Device 115 to generate an alarm. In certain embodiments, only particular mismatches trigger alarms. In some embodiments, the user may specify which target(s), and therefore which alignment dimensions, should be associated with alarms. For example, the user may desire immediate alerts for ketone and glucose levels. In such an embodiment, if the mismatch pertains to such a target, the Device 115 can generate an alarm or alert. In embodiments, the alarm can include visual prompts, sounds, vibrations, and the like to draw the user's attention. In some embodiments, the alarms, such as a ketone or glucose alarm, are provided as a real-time reminder to discourage actions such as food intake when the user is falling outside of the desired range.

In some embodiments, the Device 115 facilitates alarms, alerts, and/or information sharing to other devices or individuals. In one such embodiment, the Device 115 allows the user to share updates (automatically or on request) with one or more other devices or users. Similarly, others may subscribe or follow these updates. For example, the Device 115 may be configured to automatically share updates (e.g., analyte measurements, current and/or future states, state alignments, and the like) with others (e.g., the user's parents, doctors or other healthcare providers, and the like). In some aspects, this sharing may be triggered when the measurements (or predicted state) satisfy defined criteria (e.g., when DKA is predicted to occur or is occurring). Such sharing and following may be particularly useful to keep healthcare providers appraised of the user's status, as well as to allow others (e.g., parents of young children or young adults) to continue to monitor the health of the user.

In some embodiments, the system can provide similar alerts for repeated patterns or conditions. For example, the user (or another, such as a care provider) may configure the Device 115 to detect when a given condition or state is reached (or is predicted) above a defined frequency, above a number of times within a time period, and the like. In one such embodiment, if a user repeatedly approaches DKA or any other defined condition or state (e.g., more than three times a week), the system may alert a designated care provider (e.g., a parent or healthcare provider) to increase monitoring. For example, this may be because a diabetic user is rationing their insulin, and thereby receiving lower amounts than needed to maintain good health. By detecting such patterns and alerting others, the system can ensure that the user receives the care they need, which may include additional instruction or assistance, as well as other interventions.

In some embodiments, the system may be configured to identify when the state of the user is changing in a way that is inconsistent with the (assumed) inputs, and generate appropriate responses or alerts. This may include, for example, detection of failures of equipment, detection of dishonesty or misunderstandings in the reported actions, and the like. In one such embodiment, the system may generate alerts for the user and/or others based on inferred failures of equipment. For example, suppose the system interfaces with an insulin pump to help maintain the user's state. Suppose the system detects that the user state appears unaffected even when the pump is instructed to provide insulin (e.g., the user's levels do not change, or continue in the direction and rate they were previously moving). Based on such a detection, the system may determine that the pump is faulty, and generate an appropriate alert for the user and/or others. Similarly, if the user state appears to be changing in response to insulin even when the pump has not been instructed to provide insulin, the system may determine that the pump is leaking, and generate a corresponding alert.

Recommended Action(s)

In certain embodiments, the recommendations include one or more actions that will ameliorate any identified misalignment between goals and current and/or future states. For example, the Device 115 may suggest one or more foods to consume to ensure proper glucose and/or ketone levels, or identify alternative foods to the ones suggested or requested by the user. For example, the Device 115 may suggest "how about a handful of walnuts, instead of that cake?" As another example, the Device 115 may suggest immediate hydration and/or insulin, or immediate hospitalization, depending on the current and/or impending DKA state of the user. In certain embodiments, these actions are identified using a rules-based table. For example, the rules may specify that if ketones are too low, the appropriate action is to abstain from food. If ketones are too high, the appropriate action may be to consume food. Of course, in practice, the specific rules can be more complex, and can include a number of factors and suggestions. In another embodiment, the Device 115 identifies actions by iteratively evaluating alternatives using the Pattern(s) 125, to select action(s) that will make the future state more likely to be acceptable.

In certain embodiments, the recommendations can include both affirmative actions, as well as inaction. In at least one embodiment, the recommendations are identified by iteratively using the Pattern(s) 125 to estimate or determine the resulting states caused by taking the potential action. The resulting predictions can then be used to identify an optimal path forward. In certain embodiments, the predictions can be used to identify one or more actions that ensure or increase the probability that optimal ketosis is maintained, while minimizing any negative effects. By providing such recommendations, the system can better assist users in their decision making. That is, rather than simply predicting future states, the model can dynamically and intelligently identify actionable steps the user can take to improve those states.

In certain embodiments, the recommendations can include, for example, recommending that the user consume a meal and/or beverage, refrain from doing so, engage in a physical activity, refrain from exercise or other planned activity, and the like. In certain embodiments, if a meal is recommended or if the user requested a meal suggestion, the recommended action can include an indication of an acceptable meal type, amount, calorie amount, and the like. As discussed above, ketosis is a complex and delicate state, often requiring a careful balance of fats, proteins, and carbohydrates. Often, the balance must be meticulously followed to prevent falling out of the optimal range. In some embodiments, in addition to suggesting meal types, the decision support system can further suggest a location to get the meal. For example, the system can suggest, a restaurant name, address, and/or directions to the restaurant, and the like.

In some such embodiments, the alternatives are identified based on the current location of the user, and/or the food options that are currently available to the user. The Device 115 can then estimate impacts for each potential alternative meal. In certain embodiments, the system can identify restaurants and other food and beverage options within a predefined distance from the user. In the case of restaurants, the system may retrieve a menu for each, and evaluate the menu options to identify locations and/or menu items that can be safely consumed. In certain embodiments, the system can similarly retrieve data about food and beverages the User 105 currently possesses, such as in a fridge or pantry at home, and evaluate each such option. In this way, one or more meal options are found which will ensure or improve the probability that the future state aligns with the relevant criteria/target states.

User Interfaces

Ultimately, in certain embodiments, the decision support system outputs the determined alignments, and/or recommendations, to the user. In some embodiments, for example, the decision support system does so via the Device 115. For example, the Device 115 can update a GUI to reflect any generated alarms, provide textual suggestions, and the like. In some embodiments, the Device 115 uses audio and/or tactile feedback to output the alarms and recommendations. In at least one embodiment, the output includes natural language indicating the suggested action, rather than simply stating the action. For example, rather than simply stating "do not eat" or "eat walnuts," the output may state "if you can abstain from food for a little while, you'll be well on your way to your goals!" or "how about a nice handful of walnuts, instead of that apple?" As discussed above, ketosis requires a delicate balance and it is easy to misstep. Natural language suggestions can help comfort the user and ensure they meet their goals.

In some embodiments, the decision support system provides the output at a time when it is likely to be effective. When trying to reach ketosis, many individuals give up due to increasing hunger, before benefits are realized. In some embodiments, therefore, the decision support system can identify growing hunger. In certain embodiments, the system identifies growing hunger based on user input, and/or using the Pattern(s) 125, and preemptively suggest meal(s) to the user. This can be based on predicted future misalignment. For example, in certain embodiments the growing hunger correlates to increased probability that the user will eat, which will prevent ketosis.

In certain embodiments, the decision support system provides an integrated GUI that enables health tracking across a variety of metrics and through time. In at least one embodiment, the GUI includes a whole body dashboard reflecting a wide variety of data for the User 105. In certain embodiments, the GUI includes a body silhouette depicting the outline of a person, with various data indicated for the user. In certain embodiments, the silhouette can show the user's progress, and/or future predictions for the user. For example, the silhouette may include future predictions as separate layers overlaid on the current progress/state. In various embodiments, the GUI can include current measurements, historical trends, and/or predicted values for analytes like glucose or ketone levels, as well as weight trends, insulin sensitivity trends, fat burn, and the like. In at least one embodiment, the GUI includes a button or other input that the user can use to indicate hunger. This can allow the system to detect patterns of hunger, in correlation with the other metrics and measurements.

In some embodiments, the GUI indicates a time in range for relevant analytes. For example, the system may determine how long a user's levels of a given analyte have been within the defined optimal or preferred range, and output an indication of this time. In some embodiments, this includes how long the user has currently been in the range. In certain embodiments, this includes a cumulative value, indicating the total time in range over a period of time. In certain embodiments, the period of time can include, for example, the time in range for the day, over the last week, and the like. This may encourage the user and keep them more informed. In certain embodiments, the GUI also indicates the current and/or prior rate of change (RoC) for various analytes, such as glucose and/or ketones. This information can further inform the user about the ways their body is changing, and help them ensure their levels are maintained within desired zones.

In certain embodiments, the GUI indicates the user's progress, as compared to expected progress. For example, the GUI can display the user's actual fat burn as compared to expected fat burn. This can allow the user to identify and understand actions that work to help achieve their goals, as well as actions that do not help or actively impede progress. In at least one embodiment, the GUI can provide customizable views for the user, based on the user's goal(s). That is, based on the user goals, the system may determine what metrics are most relevant or important, and personalize the GUI to reflect these metrics more prominently. For example, if the primary user goal is to improve insulin resistance or sensitivity, the system can provide metrics relating to insulin resistance or sensitivity at the top of the GUI above the body silhouette, and allow the user to manually select and view other less important metrics, such as weight loss. In some related embodiments, the GUI provides a startup kit for the user, to help set out a plan or guide towards the user's goals. This kit can include, for example, projections about the timelines towards the goals, indications of the goals themselves, actions the user has taken and/or should take to reach the goals, and/or the user's progress toward the goals.

In certain embodiments, the decision support system can provide any number of other services and processing for users. For example, using this integrated environment, the system can determine combinations of measurements that indicate risk factors for disease states. The decision support system can then provide these metrics to the user and/or a healthcare provider to help understand markers and identify new correlations indicative of potential risks, such as sepsis, ketoacidosis, hypoglycemia, and the like.

In at least one embodiment, the system can collect information from a wide variety of users, and aggregate it to enable data mining. In embodiments, the information can first be anonymized to protect user privacy. Such aggregate data can be utilized to evaluate population health across demographics, identify risk factors for each demographic, and the like.

In certain embodiments, the decision support system may be used to visually depict patterns and trends to the user, to allow the user to easily grasp how they have changed and improved. Such patterns can include, for example, insulin and glucose sensitivity and/or tolerance, mood and mental state, physical state, hunger levels, the weight of the user, and the like. For example, in certain embodiments, an improvement metric for glucose tolerance/sensitivity can include that, as ketone levels remain in range, glucose levels tend to also stay in range despite other activities or actions that previously pushed glucose levels outside of the desired range. In some embodiments, the user can use the decision support system to set goals, and the decision support system can determine and depict the user's progress towards reaching their goals. In certain embodiments, the user goals can include, for example, goal weights, time in ketosis, and the like.

In some embodiments, the decision support system provides retrospective information, as well as state-based projections. For example, the retrospective information can include indications of what the user consumed, how much they consumed, activities the user performed, and the like. This retrospective information can further include indications of the resulting state(s), such as the ketone level. With respect to projections, in some embodiments, the system indicates, to the user, predictions about when state changes will occur. For example, this can include when the user will enter ketosis, when side effects are expected to end, expected weight loss, and the like. In certain embodiments, the side effects can include, for example, hunger, irritability, and the like.

Education

As explained herein, the ketogenic regiment is highly complex, and requires significant knowledge of the domain. In some embodiments, to reduce this barrier to entry, the GUI includes information to help educate the user and others about the ketogenic regiment. For example, in certain embodiments, the system provides articles and information about alternatives to body mass index (BMI) as a measurement of overall health. These alternatives can include the measurements collected by the system, such as ketone and glucose levels, glucose sensitivity, and the like. In a further embodiment, the system provides information regarding the health benefits of the diet. In certain embodiments, the information can include, for example, articles, studies, and the like. As discussed above, these benefits are wide ranging, and include weight loss, improved insulin resistance or sensitivity and glucose sensitivity, reduced acne, improved polycystic ovary syndrome (PCOS) symptoms, lower blood sugar and insulin levels, better diabetes management such as via lower or no insulin dependency for type 2 diabetes, improved heart health, reduced cancer and epilepsy risk, improved brain function such as improved focus and/or learning, treatment for disease such as Parkinson's, Alzheimer's, sleep disorders, etc.

In at least one embodiment, the GUI provides information to aid the education of others. For example, the user may appreciate the benefits of the regiment, but may be ill prepared to discuss the nuances and complexities of the diet with others. In certain embodiments, therefore, the GUI can provide snippets or quick tips, fun facts, articles, and the like to be shared by the user. This can dramatically improve the user's ability to maintain the diet, and encourage others to join.

In embodiments, the system can analyze the current and/or future alignment to generate any number of outputs. These outputs can include alarms, recommendations, suggestions, education materials, encouragement, and the like.

In certain embodiments, the decision support system can dynamically support the user as they begin their ketogenic regiment. As discussed above, users often feel particularly negative side effects in the early stages of the diet (often referred to as the keto flu). To help overcome these difficulties, in some embodiments, the decision support system provides guidance on easing into the diet, as discussed above. In some embodiments, the decision support system can further provide coaching and encouragement during these early stages, to ensure the user does not give up. Similarly, in certain embodiments, the decision support system provides relatively frequent updates to the user at this stage, regarding the user's progress. This can help boost motivation and keep the user on track.

Setting Goals and Expectations

In some embodiments, the decision support system acts as a platform to facilitate community interactivity. In some embodiments, this includes allowing users to support each other. In certain embodiments, the user interactions and support can include, for example, encouragement, tips, opportunities to brag about their success, and the like. In certain embodiments, this includes enabling comparisons and competitions between users. For example, the decision support system can provide a high-scores list among a group of friends, showing how each is progressing. This can help encourage the user to better maintain a ketogenic lifestyle by keeping them more engaged with their progression.

In some embodiments, the decision support system outputs metrics regarding expected progress towards one or more goals, compared to the user's actual progress towards the goal(s). For example, in certain such embodiments, the system can output the expected or predicted weight loss for the user given their metrics, demographics, actions, and the like. The system can further output the actual weight loss for the user on this timeline. In certain embodiments, the decision support system can thereby identify approaches that work best for the individual user. In at least one embodiment the system does so by identifying points in the timeline where the actual progress diverged from expected progress, and determining what user actions occurred around that time. In some embodiments, the system similarly identifies points where the user's progress began to more-closely align with the expected progress, and identify the actions occurring at these times. The decision support system can then output indications of these actions, to guide user decision making.

In certain embodiments, the decision support system tracks optimal ranges and correlations to user goals, and outputs indications of these determined optimal ranges and/or correlations. This can include ranges for optimal weight loss, improving insulin sensitivity, or any other health metric. For example, the system may identify periods in the historical data in the Pattern 125 where the user's progress was most significant. The system can then identify the analyte levels or other data associated with the user in these windows, and output an indication that these levels are desired or optimal for the user, based on past data. In certain related embodiments, the system can similarly use this analysis to perform efficiency tracking, and output an indication of how efficiently the user is towards their goal(s) at any given time. In certain embodiments, the system can further optimize suggestions to ensure the user takes an efficient path towards their goal(s), based on prior data. For example, the system may indicate to the user that they could achieve their goal faster by performing certain activities, refraining from eating certain things, and the like. In some embodiments, the system can learn and indicate that the user can increase their food consumption in some instances while still remaining on track to reach their goals.

In certain embodiments, the system can use this efficiency analysis to guide the user towards optimal weight loss levels. For example, based on identified correlations between actions, measurements, and weight loss, the system can identify actions and/or meals that are associated with high or otherwise optimal weight loss. The system can then provide, to the user, instructions or suggestions to reach these optimal levels again. In some embodiments, the system similarly guides the user towards optimal results for other health metrics, such as insulin sensitivity.

In some embodiments, in addition to identifying and providing the optimal range(s), the system further guides the user back into optimal ranges when needed. In certain embodiments, the system uses the pattern(s) to identify latency/time lags between actions and impacts, and/or rates of change in analytes, to guide the user back into the range. For example, based on the delay between an action, such as eating or exercising, and the resulting shift in ketones, the system can instruct the user on what actions to take, and when to take them, to re-enter the optimal range. In some embodiments, to help decide what actions to take and when to take them, the system further guides the user based on the current rate of change in ketones.

In at least one embodiment, the decision support system can provide a customizable path for the user towards ketosis or another state. Often, individuals have difficulty transitioning from their ordinary diets to a ketogenic diet. To aid this transition, therefore, the decision support system can evaluate the user's current habits, and propose gradual changes to ease the user into ketosis overtime. In certain embodiments, the changes are designed to ease the user in to the diet over a user-specified period of time. For example, the decision support system may generate a custom path that will gradually take the user from their current habits to a fully ketogenic life in one week, one month, etc. This can include, for example, suggested foods on various day throughout the week, as well as at various points in the day, to minimize the initial hunger and other negative effects, while ensuring the transition to ketosis is achieved. In at least one embodiment, this customized path includes a target length of time to be spent in ketosis on a given day, with the time slowly ramping up to the final goal.

As an example of a customizable path, suppose a user currently consumes carbohydrate-laden food twice a day, on average. A typical ketogenic regimen will likely require the user to significantly reduce this carbohydrate intake (or perhaps eliminate entirely), especially if the user is male. However, immediately reducing carbohydrate intake to zero is likely to cause other side effects for the user, including fatigue, headaches, difficulty with attention, aches, and general frustrations. A custom path, therefore, may be generated to slowly ease the user into the diet. This may include instructing the user to consume carbohydrates once a day at a specified time, rather than twice a day. Eventually, the instructions can shift to no carbohydrates, as needed. As another example, suppose the user currently exercises once a week, but the system determines that three times a week would be more optimal. In certain embodiments, the system can ask the user to gradually increase their workouts for a period of time, until the optimal level is reached. In certain embodiments, the increased workouts may include, for example, working out more than one day per week, engaging in progressively longer workouts each day, and the like.

Figure 8:
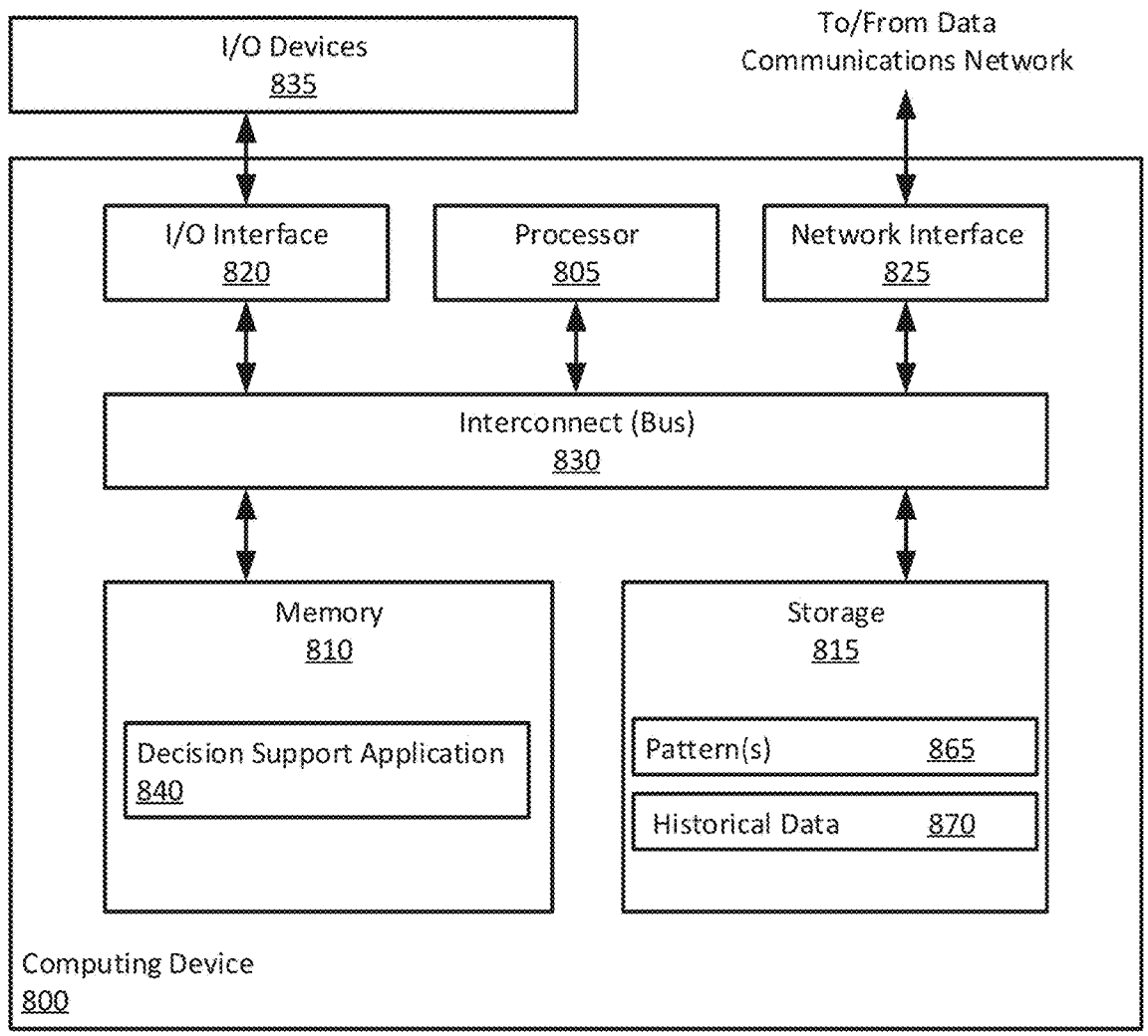
FIG. 8 is a block diagram depicting a computing device configured to analyze user data to aid decision-making, according to certain embodiments disclosed herein.

FIG. 8 is a block diagram depicting a Computing Device 800 configured to analyze user data to aid decision-making, according to certain embodiments disclosed herein. Although depicted as a physical device, in embodiments, the Computing Device 800 may be implemented using virtual device(s), and/or across a number of devices, such as in a cloud environment. As illustrated, the Computing Device 800 includes a Processor 805, Memory 810, Storage 815, a Network Interface 825, and one or more I/O Interfaces 820.

In the illustrated embodiment, the Processor 805 retrieves and executes programming instructions stored in Memory 810, as well as stores and retrieves application data residing in Storage 815. The Processor 805 is generally representative of a single CPU and/or GPU, multiple CPUs and/or GPUs, a single CPU and/or GPU having multiple processing cores, and the like. The Memory 810 is generally included to be representative of a random access memory. Storage 815 may be any combination of disk drives, flash-based storage devices, and the like, and may include fixed and/or removable storage devices, such as fixed disk drives, removable memory cards, caches, optical storage, network attached storage (NAS), or storage area networks (SAN). The Computing Device 800 shown in FIG. 8 is merely an example device, and certain elements may be modified or removed, and/or other elements or equipment may be added.

In some embodiments, Input and Output (I/O) Devices 835 (such as keyboards, monitors, etc.) can be connected via the I/O Interface(s) 820. Further, via the Network Interface 825, the Computing Device 800 can be communicatively coupled with one or more other devices and components. In certain embodiments, the Computing Device 800 is communicatively coupled with other devices via a network, which may include the Internet, local network(s), and the like. The network may include wired connections, wireless connections, or a combination of wired and wireless connections. As illustrated, the Processor 805, Memory 810, Storage 815, Network Interface(s) 825, and I/O Interface(s) 820 are communicatively coupled by one or more Interconnects 830. In certain embodiments, the Computing Device 800 is representative of the Device 115 associated with the user. In certain embodiments, as discussed above, the Device 115 can include the user's laptop, computer, smartphone, and the like. In another embodiment, the Computing Device 800 is a server executing in a cloud environment.

In the illustrated embodiment, the Storage 815 includes one or more Patterns 865, and one or more sets of Historical Data 870. In certain embodiments, if the Computing Device 800 is operating in a cloud environment, it may maintain any number of Patterns 865 and sets of Historical Data 870. For example, the Storage 815 can include a separate personalized Pattern 865 and a separate set of Historical Data 870 for each user associated with the system.

Additionally, in certain embodiments, the Storage 815 includes one or more collective Patterns 865 and/or sets of Historical Data 870. For example, there may be a generic/default Pattern 865 to be used for users that do not have personalized models or data available. In a related embodiment, the Storage 815 can include demographic-specific Patterns 865, to be used for users who have provided demographic information, but who do not have sufficient personal data in the Historical Data 870. As discussed above, the Patterns 865 are generally used to evaluate data from users in order to predict future states, and/or suggest optimal actions.

In some embodiments, the Historical Data 870 generally includes data associated with the user(s), collected over a period of time. In certain embodiments, the Historical Data 870 includes a set of records, each indicating the state of a user at a given point in time, along with an identifier of the user and an indication of the time/date associated with the record. The state can include, for example, the current biological and/or mental state of the user, actions the user recently or is actively engaged in at the time, and the like. In certain embodiments, the Historical Data 870 further includes an indication of the action(s) that were suggested by the Computing Device 800, given the other data in the record.

As illustrated, the Memory 810 includes a Decision Support Application 840. Although depicted as software residing in Memory 810, in embodiments, the functionality of the Decision Support Application 840 can be implemented using hardware, software, or a combination of hardware and software. In certain embodiments, the Decision Support Application 840 performs various aspects of the support and decision-making functionality described above.

Each of these non-limiting examples can stand on its own or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system comprising:
   a sensor configured to generate, on at least a defined interval and without user intervention, one or more current measurements associated with one or more current levels of an analyte for a user, wherein the one or more current levels of the analyte are correlated to a current level of ketones of the user;
   a memory circuit storing one or more past measurements of one or more past levels of the analyte for the user, wherein the one or more past levels of the analyte are correlated to one or more past levels of ketones of the user; and
   a processor in data communication with the sensor and the memory circuit, the processor configured to:
      receive, from the sensor, the one or more current measurements;
      determine, for a time period comprising a first period portion and a second period portion, a rate of change over time of an analyte level of the user, wherein the determination of the rate of change is based on the one or more past measurements and the one or more current measurements, the one or more past measurements corresponding to the first period portion and the one or more current measurements corresponding to the second period portion;
      generate a pattern based on the rate of change;
      determine a first alignment with a first user target based on the generated pattern, wherein the first user target relates to one or more of a mental state or physical state of the user; and
      output a first result to the user, based on the determined first alignment.

2. The system of claim 1, wherein the one or more current levels comprise one or more of a glucose level, a lactate level, or a ketone level.

3. The system of claim 1, wherein the first result comprises a recommendation of an action.

4. The system of claim 3, wherein the recommendation of the action comprises one or more of a recommendation to refrain from eating one or more foods, a recommendation to eat one or more foods, a recommendation to partake in one or more activities, or a recommendation to refrain from one or more activities.

5. The system of claim 1, wherein the processor is configured to output the first result in a user interface indicating one or more of a current ketone state of the user or a predicted future ketone state of the user.

6. The system of claim 1, wherein the processor is configured to output the first result in a user interface indicating one or more of a current weight of the user or a predicted future weight of the user.

7. The system of claim 1, wherein the processor is configured to output the first result in a user interface indicating one or more of a current mental state of the user or a predicted future mental state of the user.

8. The system of claim 1, wherein the processor is further configured to:
   refine the pattern based on the one or more current measurements;
   receive one or more additional measurements of one or more additional levels of the analyte for the user; and
   determine a second alignment with the first user target based on the refined pattern.

9. The system of claim 1, wherein the one or more past measurements are correlated with one or more past mental states, wherein the first user target relates to the mental state, and wherein the first result comprises a predicted mental state of the user.

10. The system of claim 1, wherein the processor is further configured to:
    receive an indication of a physical activity associated with the user; and
    generate the pattern further based on the indication of the physical activity.

11. The system of claim 1, wherein the first user target relates to a ketone level.

12. The system of claim 1, wherein the first result indicates whether or not the first user target is predicted to he met at a future time.

13. The system of claim 1, wherein, to generate the pattern, the processor is configured to:
    generate a trend line for the user, based on the determined rate of change; and
    estimate a future state of the user, based on the trend line.

14. The system of claim 1, wherein the processor is further configured to:
    identify a plurality of user targets associated with the user, wherein the plurality of user targets comprise user-specified targets with respect to (i) weight loss, (ii) mental health, (iii) glucose level, (iv) insulin sensitivity, and (v) glucose sensitivity.

15. The system of claim 1, wherein, to determine the first alignment with the first user target, the processor is configured to:
    determine whether a current state of the user aligns with the first user target; and
    determine whether a predicted future state of the user aligns with the first user target.

16. The system of claim 15, wherein the processor is farther configured to:
in response to determining that the predicted future state of the user does not align with the first user target, generate a first recommendation, wherein the first recommendation includes an action that will increase a probability that the predicted future state will align with the first user target, and wherein the first result comprises the first recommendation.

17. A computer-implemented method, comprising:
receiving, at a processor, from a sensor, one or more current measurements associated with one or more current levels of an analyte for a user, wherein the sensor generates the one or more current measurements on at least a defined interval and without user intervention;
storing, at a memory circuit, one or more past measurements of one or more past levels of the analyte for the user, wherein the one or more past levels of the analyte are correlated to one or more past levels of ketones of the user;
determining, at the processor, for a time period comprising a first period portion and a second period portion, a rate of change over time of an analyte level of the user, wherein the determining of the rate of change is based on the one or more past measurements and the one or more current measurements, the one or more past measurements corresponding to the first period portion and the one or more current measurements corresponding to the second period portion;
generating, at the processor, a pattern based on the rate of change;
determining, at the processor, a first alignment with a first user target based on the generated pattern, wherein the first user target relates to one or more of a mental state or physical state of the user; and
outputting, at the processor, a first result to the user, based on the determined first alignment.

18. The computer-implemented method of claim 17, further comprising:
refining the pattern based on the one or more current measurements;
receiving one or more additional measurements of one or more additional levels of the analyte for the user; and
determining a second alignment with the first user target based on the refined pattern.

19. The computer-implemented method of claim 17, wherein generating the pattern comprises:
generating a trend line for the user, based on the determined rate of change; and
estimating a future state of the user, based on the trend line.

20. A non-transitory computer-readable storage medium encoded with instructions operable to configure an electronic device to perform an operation, the operation comprising:
receiving, at a processor, from a sensor, one or more current measurements associated with one or more current levels of an analyte for a user, wherein the sensor generates the one or more current measurements on at least a defined interval and without user intervention;
storing, at a memory circuit, one or more past measurements of one or more past levels of the analyte for the user, wherein the one or more past levels of the analyte are correlated to one or more past levels of ketones of the user;
determining, at the processor, for a time period comprising a first period portion and a second period portion, a rate of change over time of an analyte level of the user, wherein the determining of the rate of change is based on the one or more past measurements and the one or more current measurements, the one or more past measurements corresponding to the first period portion and the one or more current measurements corresponding to the second period portion;
generating, at the processor, a pattern based on the rate of change;
determining, at the processor, a first alignment with a first user target based on the pattern, wherein the first user target relates to one or more of a mental state or physical state of the user; and
outputting, at the processor, a first result to the user, based on the determined first alignment.

* * * * *